US005583235A

United States Patent [19]
Bierer et al.

[11] Patent Number: 5,583,235
[45] Date of Patent: Dec. 10, 1996

[54] PREPARATION OF SYMMETRICAL AND UNSYMMETRICAL 3,6-DISUBSTITUTED-1,2-DITHIINS HAVING ANTIFUNGAL ACTIVITY

[75] Inventors: Donald E. Bierer; Jeffrey M. Dener, both of Daly City; Thien V. Truong, Emeryville, all of Calif.

[73] Assignee: Shaman Pharmaceuticals, Inc., San Francisco, Calif.

[21] Appl. No.: 212,096

[22] Filed: Mar. 11, 1994

[51] Int. Cl.$^6$ ................................................. C07D 339/08
[52] U.S. Cl. .............................................. 549/20; 549/22
[58] Field of Search .......................................... 549/20, 22

[56] References Cited

U.S. PATENT DOCUMENTS

| | | | |
|---|---|---|---|
| 4,659,733 | 4/1987 | DuPriest et al. | 514/436 |
| 5,202,348 | 4/1994 | Towers et al. | 514/436 |

FOREIGN PATENT DOCUMENTS

| | | | |
|---|---|---|---|
| 2118437 | 10/1972 | Germany | 514/436 |

OTHER PUBLICATIONS

Chemical Abstracts, vol. 77, No. 1, Abstract No. 4826n, p. 433, Jul. 3, 1972, Reid et al.
E. Block et al., "Total Synthesis of Thiarubrine B [3–(3–Buten–1–ynyl)–6–(1,3–pentadiynyl)–1,2–dithiin], The Antibiotic Principle of Giant Ragweed (*Ambrosia trifida*)", J. Am. Chem. Soc. 116:9403 (1994).
T. W. Greene et al., "Protective Groups in Organic Synthesis", John Wiley & Sons, Inc., New York, 1991, p. 296.
Freeman and Kim, 1989, "The Chemistry of 1,2–Dithiins," *Sulfur Reports* 9(3):207–256.
Koreeda and Yang, Mar. 1994, "The Chemistry of 1,2–Dithiins: Synthesis of 1,2–Dithiin and 3,6–Disubstituted 1,2–Dithiins," *Synlett* 201–203.
Schroth et al., 1967, "1,2–Dithiins, a New Type of Heterocycle", Angew Chem, Int Ed Eng 6:698–699.
Schroth et al., 1966, "Stereoisomeric 1,4–dimercaptobutadiene", Chemical Abstracts vol. 64, Abstract 3339a.
Mao et al., 1994, "In vitro Evaluation of a Series of Novel Substituted 1,2–Dithiins", XII Congress of the International Society for Human and Animal Mycology, Adelaide, South Australia, Mar. 13–18.
Yang and Koreeda, 1993, American Chemical Society, Division of Organic Chemistry, 206th National Meeting, Aug. 22–27 1993, Abstract 349.
Koreeda and Yang, 1994, "Chemistry of 1,2–Dithiins. Synthesis of the Potent Antibiotic Thiarubrine A", J Am Chem Soc 116:10793–10794.
Freeman et al., 1993, "Naturally Occurring 1,2–Dithiins" in Reviews on Heteroatom Chemistry; Oae, S., Ed., Tokyo pp. 1–19.
Hudson et al., 1993, "Light–Mediated Activities of Thiarubrines Against Human Immunodeficiency Virus", Photochemistry and Photobiology 57:675–680.
Ellis et al., 1993, "A Diathiacyclohexadiene Polyyne Alcohol from *Ambrosia Chamissonis*", Phytochemistry 33:224–228.
Gomez–Barrios et al., 1992, "Studies on the Biosynthesis of Thiarubrine A in Hairy Root Cultures of *Ambrosia Artemisiifolia* Using $^{13}$C–Labelled Acetates", Phytochemistry 31:2703–2707.
Cimiraglia et al., 1991, "An ab initio Study of the Structure and Electronic Spectrum of 1,2–Dithiete and 1,2–Dithiin", J Mol Struct (Therochem). 230:287–293.
Aihara et al., 1990, "Chemical Evolution, Biosynthesis, and Aromaticity", J Bull Chem Soc Jpn, 63:2899–2903.
Balza et al., 1990, "Dithiacyclohexadiene Chlorohydrins and Related Sulphur Containing Polyynes from *Ambrosia Chamissonis*", Phytochemistry 29:2901–2904.
Balza et al., 1989, "Dithiacyclohexadienes and Thiophenes from *Ambrosia Chamissonis*", Phytochemistry 28(12):3523–3524.
Constabel et al., 1989, "Incorporation of $^{35}$S into Dithiacyclohexadiene and Thiophene Polyines in Hairy Root Cultures of *Chaenactis Douglasii*", Phytochemistry 28:93–95.
Constabel et al., 1989, "The Complex Nature of the Mechanism of Toxicity of Antibiotic Dithiacyclohexadiene Polyines (Thiarubrines) from the Asteraceae", Planta Med 55:35–37.
Fabian and Birner, 1988, "A Theoretical Study of the Disulfide/Dithione Valence Isomerism", Coll Czech Chem Comm 53:2096–2115.
Hudson et al., 1986, "Comparison of the Antiviral Effects of Naturally Occurring Thiophenes and Polyacetylenes", N Planta Medica 52:453–457.
Hudson et al., 1986, "Antiviral Properties of Thiarubrine–A, a Naturally Occurring Polyine", Planta Med 52:51–54.
Cosio et al., 1986, "Production of Antibiotic Thiarubrines by a Crown Gall Tumor Line of *Chaenactis douglasii*", J Plant Physiol 124:155–164.
Towers et al., 1985, "Antibiotic Properties of Thiarubrine A, a Naturally Occurring Dithiacyclohexadiene Polyine", Planta Medica 51:225–229.
Rodriguez et al., 1985, "Thiarubrine A, a Bioactive Constituent of *Aspilia* (Asteraceae) Consumed by Wild Chimpanzees", N Experimenta 41:419–420.
Kokwaro, 1976, Medicinal Plants of East Africa, East African Literature Bureau, pp. 58–76.

(List continued on next page.)

*Primary Examiner*—Zinna Northington Davis
*Attorney, Agent, or Firm*—Pennie & Edmonds

[57] ABSTRACT

The present invention provides an improved procedure for the preparation of 3,6-disubstituted-1,2-dithiin derivatives, especially unsymmetrical 1,2-dithiins. In addition, the process offers significant process, scaleup, and safety advantages over the previously reported synthetic processes. The compounds synthesized by this new process and described herein are particularly effective in treating fungal infections, especially those caused by *Candida albicans, Cryptococcus neoformans, Aspergillus fumigatus, Trichophyton rubrum, Candida parapsilosis, Candida tropicalis,* or *Candida krusei.*

16 Claims, No Drawings

OTHER PUBLICATIONS

Ried and Ochs, 1972, "Electrophilic Addition of Disulfur Dichloride (S2Cl2 to Alkynes)", Chemical Abstracts 77:433, Abstract 4826m.

Bohlmann and Kleine, 1965, "Uber rote Naturliche Schwefelacetylenverbindungen", M Chem Ber 98:3081–3086.

Mortensen et al., 1964, "Studies Related to Naturally Occurring Acetylene Compounds", Acta Chem Scand 18:2392–2394.

Dzhemilev et al., 1986, "A new catalytic reaction of elemental sulfur with acetylenes by the action of cobalt complexes", Izh. Akad. Nauk SSSR, Ser. Khim. 5:1211–1212.

Dzhemilev et al., 1987, "An original method for the preparation of sulfides and disulfides involving cobalt complexes", Izh. Akad. Nauk SSSR, Ser. Khim. 8:1918.

PREPARATION OF SYMMETRICAL AND UNSYMMETRICAL 3,6-DISUBSTITUTED-1,2-DITHIINS HAVING ANTIFUNGAL ACTIVITY

TABLE OF CONTENTS

1. FIELD OF THE INVENTION

2. BACKGROUND OF THE INVENTION

3. SUMMARY OF THE INVENTION

4. Detailed Description of the Invention 4.1 Total synthesis of the 1,2-Dithiin Derivatives
   4.2 Novel Compounds
   4.3 Methods of Use

5. EXAMPLES 5.1 General Experimental Section
   5.2 Examples

1. FIELD OF THE INVENTION

This invention pertains to a novel and versatile methodology for the preparation of a new group of 1,2-dithiin heterocyclic compounds that are useful in slowing fungal growth and killing fungi. Furthermore these novel 1,2-dithiin containing substances have beneficial antiviral and antibacterial properties.

2. BACKGROUND OF THE INVENTION 1,2-Dithiins are six-membered heterocycles having a disulfide linkage in place of the two contiguous CH groups of benzene. The 1,2-dithiin class of heterocycles have been of interest due to their interesting physical and biological properties. This is due to the fact that eight natural products containing this unique heterocycle have been isolated since the 1960's, primarily from plants of the family Asteraceae. Among these natural products is thiarubrine A, isolated from leaves of *Aspilia mossambicesis* and *A. plurisetta*, which has been shown to possess both antifungal and antiviral activity, but is also cytotoxic (Constabel, C. P.; Towers, G. H. N. *Planta Med.* 1989, 55, 35–37; Hudson, J. B.; Graham, E. A.; Finlayson, A. J.; Towers, G. H. N. *Planta Med.* 1986, 52, 51–54; Towers, G. H. N.; Abramowski, Z.; Finlayson, A. J.; Zucconi, A. *Planta Medica* 1985, 3, 225–229). Other thiarubines which possess antifungal and antibacterial activity have been described ((Towers, G. H. N.; Balza, F.; Abramowski, Z. A.; Lopez-Bazzochi, I. U.S. Pat. No. 5,202, 348, Apr. 13, 1993). These compounds are both heat and light sensitive, and easily convert to the corresponding thiophenes under proper thermal or photochemical conditions. All of the natural products possess acetylenic sidechains in the 3- and 6-positions of the dithiin, which may in part account for their instability. Additionally, compounds related to dithiins have been known to possess antiviral, antibacterial and antifungal activities (Hudson, J. R.; Graham, E. A.; Chan, G.; Finlayson, A. J.; Towers, G. H. N. *Planta Med.* 1986, 52, 453; Cosio, E. G.; Norton, R. N.; Towers, E; Finlayson, A. J.; Rodriguez, E.; Towers, G. H. N. *J. Plant Physiol*, 1986 124, 155–164).

No reports of the total synthesis of any naturally occurring thiarubrines have appeared in the literature, possibly due to the thermal and photochemical instability of these molecules. Furthermore, no biological data for the 3,6-disubstituted-1,2-dithiins without the acetylenes has been reported prior to the recent disclosure by the current inventors in August 1993 (Truong, T. V.; Bierer, D. E.; Dener, J. M.; Hector, R.; Tempesta, M. S.; Loev, B.; Yang, W.; Koreeda, M. U.S. patent application, filed Aug. 24, 1993, which discloses antifugal activity of non-acetylene 3,6-disubstituted-1,1-dithiins. See also Abstract 349 of W. Yang and M. Koreeda, American Chemical Society, Division of Organic Chemistry, 206 National Meeting, Aug. 22–17, 1993). Due to the natural products' inherent cytotoxicity and extreme instability to light, these substances are not well-suited for use as therapeutic agents. In an effort to avoid these limitations, a series of novel symmetrical and unsymmetrical dithiins were synthesized and their antifungal properties were determined.

Schroth and coworkers (Schroth, W.; Billig, F.; Reinhold, G. Angew. *Chem., Int. Ed. Engl.* 1969, 6, 698) reported the first preparation of the parent 1,2-dithiin and 3,6-disubstituted analogues in the 1960's. Truong et al. (Truong, T. V.; Bierer, D. E.; Dener, J. M.; Hector, R.; Tempesta, M. S.; Loev, B.; Yang, W.; Koreeda, M. U.S. patent application, filed Aug. 24, 1993) synthesized a number of 3,6-disubstituted dithiin analogues, including some diester derivatives, using a synthetic process which is a modification to that described by Schroth. This synthetic process involves the addition of benzyl mercaptan to a 1,4-diaryl-1,3-diacetylene, followed by reduction of the benzyl groups with sodium in ammonia and oxidation of the sulfide anions to the dithiin with iodine or potassium ferricyanide. Although this method was most useful for the preparation of 3,6-diaryl-1,2-dithiins, it is less satisfactory for the synthesis of 1,2-dithiins with substituents other than aromatic rings in the 3- and 6-positions of the dithiin. Furthermore the process is unattractive for large scale reactions since it involves the use of liquid ammonia and reactive alkali metals which may be hazardous to handle in large quantities.

Citation or identification of any reference in Section 2 of this application shall not be construed as an admission that such reference is available as prior art to the present invention.

3. SUMMARY OF THE INVENTION

The invention is devoted to a new and versatile process for the synthesis of antifungal, antiviral and antibacterial compounds of the following formula

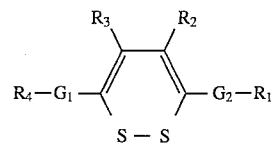

where $R_2$ and $R_3$ are hydrogen;

$G_1$ and $G_2$ are independent of each other and not necessarily equal to each other, but in some instances can be equal to each other. $G_1$ and $G_2$ can be an alkyl or branched alkyl radical comprising 1 to 10 carbon atoms, or a cycloalkyl radical comprising 3 to 10 carbon atoms;

$R_1$ and $R_4$ are independent of each other and not necessarily equal to each other, but in some instances can be equal to each other. $R_1$ and $R_4$ can be defined as hydrogen, azido, cyano, formyl, halogen, $OR_5$, $SR_6$, $COR_7$, $CO_2R_8$, $NR_9R_{10}$, or $COHNR_{11}R_{12}$ or

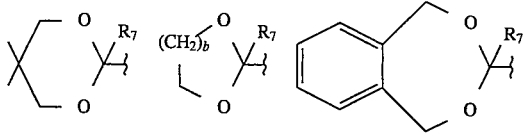

where b is an integer from 1–3;

$R_5$ is defined as hydrogen, an alkyl or branched alkyl radical comprising 1 to 10 carbon atoms, a cycloalkyl radical of 3 to 10 carbon atoms, a protecting group as described in "Protecting Groups in Organic Synthesis" by Theodora Greene and Peter G. M. Wuts, John Wiley and Sons, New York, 1991 ("Greene et al.") or an acyl radical of the type

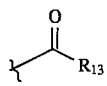

where $R_{13}$ is methyl, ethyl, cyclopropyl, propyl, 1-(methyl)ethyl, cyclobutyl, cyclopentyl, an alkyl or branched alkyl radical comprising 1 to 20 carbon atoms, a cycloalkyl radical of 3 to 20 carbon atoms, an aryl or heteroaryl ring of the type

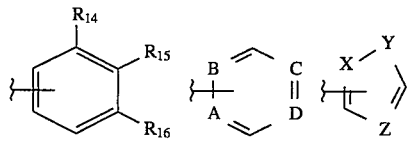

where $R_{14}$, $R_{15}$, and $R_{16}$ can be independently defined as hydrogen, an alkyl, or branched alkyl radical comprising 1 to 10 carbon atoms, a cycloalkyl radical comprising 3 to 10 carbon atoms, halogen, $OR_{17}$, $S(O)_aR_{18}$, $NR_{19}R_{20}$, $CO_2R_{21}$, $CONR_{22}R_{23}$; and A, B, C and D can be the same or different, and are independently defined as N or CH; X and Z can be the same or different and are independently defined as N or CH; and Y is O, S, or $NR_{24}$ where $R_{17}$ is hydrogen, an alkyl or branched alkyl radical comprising 1 to 10 carbon atoms, a cycloalkyl radical comprising 3 to 10 carbon atoms, a protecting group as described in Greene et al., phenyl, optionally substituted phenyl, phenylmethyl, or optionally substituted phenylmethyl;

a is and integer from 0 to 2;

$R_{18}$ is hydrogen, an alkyl or branched alkyl radical comprising 1 to 10 carbon atoms, a cycloalkyl radical comprising 3 to 10 carbon atoms, a protecting group as described in Greene et al., phenyl, optionally substituted phenyl, phenylmethyl, optionally substituted phenylmethyl; or $R_{18}$ can also be $NR_{19}R_{20}$ where $R_{19}$ and $R_{20}$ can be the same or different, or be an alkyl ring of 2 to 10 carbon atoms; $R_{19}$ can be hydrogen, an alkyl or branched alkyl radical comprising 1 to 10 carbons atoms, or a cycloalkyl radical of 3 to 10 carbon atoms, phenyl, optionally substituted phenyl, phenylmethyl, optionally substituted phenylmethyl, or a protecting group as described in Greene et al.; $R_{20}$ can be hydrogen, an alkyl or branched alkyl radical comprising 1 to 10 carbon atoms, a cycloalkyl radical of 3 to 10 carbon atoms, phenyl, optionally substituted phenyl, phenylmethyl, or optionally substituted phenylmethyl;

$R_{21}$ is defined as hydrogen, methyl, ethyl, 1-(methyl)ethyl, n-propyl, alkyl or branched alkyl radical comprising 1 to 10 carbon atoms, or a cycloalkyl radical of 3 to 10 carbon atoms, phenyl, optionally substituted phenyl, phenylmethyl, optionally substituted phenylmethyl, or a protecting group as described in Greene et al.;

$R_{22}$ and $R_{23}$ can be the same or different, or be a part of a ring of 2 to 10 carbon atoms; $R_{22}$ can be hydrogen, an alkyl or branched alkyl radical comprising 1 to 10 carbon atoms, a cycloalkyl radical of 3 to 10 carbon atoms, phenyl, optionally substituted phenyl, phenylmethyl, optionally substituted phenylmethyl, or a protecting group as described in Greene et al.;

$R_{23}$ can be hydrogen, an alkyl or branched alkyl radical comprising 1 to 10 carbon atoms, a cycloalkyl radical of 3 to 10 carbon atoms, phenyl, optionally substituted phenyl, phenylmethyl, optionally substituted phenylmethyl;

$R_{24}$ is defined as hydrogen, an alkyl or branched alkyl radical comprising 1 to 10 carbon atoms, a cycloalkyl radical of 3 to 10 carbon atoms, a protecting group as described in Greene et al., phenyl, optionally substituted phenyl, phenylmethyl, optionally substituted phenyl;

$R_{13}$ can also be $NR_{25}R_{26}$ where $R_{25}$ and $R_{26}$ can be the same or different, and $R_{25}$ and $R_{26}$ together can be an alkyl ring comprising 2 to 10 carbon atoms; $R_{25}$ can be hydrogen, an alkyl or branched alkyl radical comprising 1 to 10 carbon atoms, a cycloalkyl radical of 3 to 10 carbon atoms, a protecting group as described in Greene et al., phenyl, optionally substituted phenyl, phenylmethyl or optionally substituted phenylmethyl;

$R_{26}$ can be hydrogen, an alkyl or branched alkyl radical comprising 1 to 10 carbon atoms, a cycloalkyl radical of 3 to 10 carbon atoms, or an aryl radical of the type

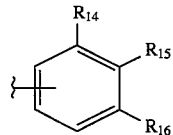

where $R_{14}$, $R_{15}$, and $R_{16}$ are as defined above;

$R_{25}$ can also be $SO_2R_{27}$ or $P(O)(OR_{28})_2$ where $R_{27}$ is an alkyl or branched alkyl radical comprising 1 to 10 carbon atoms, a cycloalkyl radical of 3 to 10 carbon atoms; $R_{27}$ can also be an aryl radical of the type

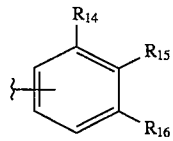

where $R_{14}$, $R_{15}$, and $R_{16}$ are as defined above, and $R_{28}$ can be hydrogen, an alkyl or branched alkyl radical comprising 1 to 10 carbon atoms, a cycloalkyl radical comprising 3 to 10 carbon atoms, phenyl, optionally substituted phenyl, phenylmethyl, or a protecting group as described in Greene et al.

$R_5$ can also be an aryl radical of the type

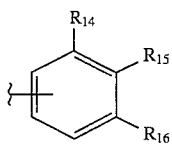

where $R_{14}$, $R_{15}$ and $R_{16}$ are as defined above;

$R_6$ can be the same as or different from $R_5$ and is defined as hydrogen, an alkyl or branched alkyl radical comprising 1 to 10 carbon atoms, a cycloalkyl radical of 3 to 10 carbon atoms, a protecting group as described in Greene et al., or an acyl radical of the type

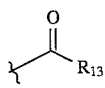

where $R_{13}$ is defined as above;

$R_6$ can also be an aryl radical of the type

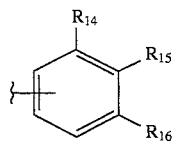

where $R_{14}$, $R_{15}$ and $R_{16}$ are as defined above;

$R_7$ is defined as methyl, ethyl, 1-(methyl)ethyl, n-propyl, an alkyl, branched alkyl or a cycloalkyl radical of 4 to 20 carbon atoms, phenyl, optionally substituted phenyl, or a protecting group as described in Greene et al.;

$R_7$ can also be an aryl radical of the type

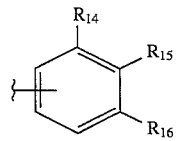

where $R_{14}$, $R_{15}$ and $R_{16}$ are as defined above;

$R_8$ is defined as hydrogen, methyl, ethyl, 1-(methyl)ethyl, phenylmethyl, optionally substituted phenylmethyl, n-propyl; an alkyl, branched alkyl, or a cycloalkyl radical of 4 to 20 carbon atoms or a protecting group as described in Greene et al.;

$R_9$ and $R_{10}$ can be the same or different, or are together an alkyl ring comprising 2 to 10 carbon atoms; $R_9$ can be hydrogen, an alkyl or branched alkyl radical comprising 1 to 10 carbon atoms, or a cycloalkyl radical of 3 to 10 carbon atoms, or a protecting group as described in Greene et al.; or $R_9$ can also be defined as $OR_{29}$ where $R_{29}$ can be hydrogen, an alkyl or branched alkyl radical of 1 to 10 carbon atoms, a cycloalkyl radical comprising 3 to 10 carbon atoms, a protecting group as described in Greene et al., phenyl, optionally substituted phenyl, phenylmethyl or optionally substituted phenylmethyl, $R_{10}$ can be defined as hydrogen; an alkyl, branched alkyl, or a cycloalkyl radical of 1 to 10 carbon atoms; or an acyl radical of the type

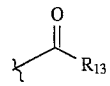

where $R_{13}$ is as defined above;

$R_{10}$ is defined as hydrogen, an alkyl or branched alkyl radical comprising 1 to 10 carbon atoms, a cycloalkyl radical of 3 to 10 carbon atoms, or an acyl radical of the type

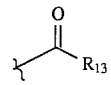

where $R_{13}$ is as defined above;

$R_{10}$ can also be $S(O)_xR_{30}$ where x is an integer from 0 to 2; and $R_{30}$ is defined as an alkyl or branched alkyl radical comprising 1 to 10 carbon atoms, a cycloalkyl radical comprising 3 to 10 carbon atoms, phenylmethyl, optionally substituted phenylmethyl, or an aryl or heteroaryl radical of the type

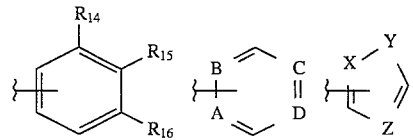

where $R_{14}$, $R_{15}$, $R_{16}$, A, B, C, D, X, Y, and Z are as defined above;

$NR_9R_{10}$ can also be defined as a radical of the type

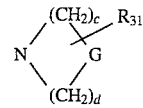

where c is an integer from 0 to 10;

d is an integer from 1 to 10;

$R_{31}$ is an alkyl, branched alkyl, or a cycloalkyl radical comprising 1 to 10 carbon atoms; an aryl or heteroaryl radical of the type

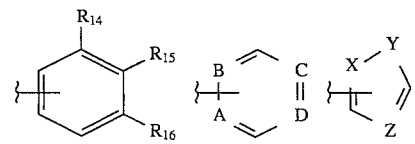

where $R_{14}$, $R_{15}$, $R_{16}$, A, B, C, D, X, Y, and Z are as defined above;

$R_{31}$ can also be $OR_{32}$, $SR_{33}$ or $NR_{34}R_{35}$ where $R_{32}$ is defined as hydrogen; an alkyl or branched alkyl radical comprising 1 to 10 carbon atoms, a cycloalkyl radical of 3 to 10 carbon atoms, a protecting group as described in Greene et al., or an acyl radical of the type

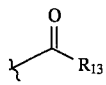

where

R$_{13}$ is as defined above;

R$_{33}$ is defined as hydrogen; an alkyl, branched alkyl, or a cycloalkyl radical of 1 to 10 carbon atoms; a protecting group as described in Greene et al., or an acyl radical of the type

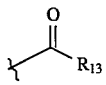

R$_{13}$ is as defined above;

R$_{34}$ and R$_{35}$ can be independently defined as hydrogen, alkyl, branched alkyl, or a cycloalkyl radical of 1 to 10 carbon atoms; a protecting group as described in Greene et al.;

G is —CH$_2$—, oxygen, a heteroatom of the type S(O)$_e$, or NR$_{36}$, where e is an integer from 0 to 2; and R$_{36}$ is defined as hydrogen, an alkyl or branched alkyl radical comprising 1 to 10 carbon atoms, a cycloalkyl radical comprising 1 to 10 carbon atoms, a protecting group as described in Greene et al.; or an acyl radical of the type

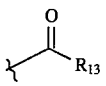

where

R$_{13}$ is defined above; or R$_{36}$ can be

S(O)$_x$R$_{30}$ where x and R$_{30}$ are defined above.

R$_{11}$ and R$_{12}$ can be the same or different or be part of a ring comprising 2 to 10 carbon atoms; R$_{11}$ can be hydrogen, an alkyl or branched alkyl radical comprising 1 to 10 carbon atoms, a cycloalkyl radical of 3 to 10 carbon atoms, or a protecting group as described in Greene et al.;

R$_{11}$ can also be defined as OR$_{37}$ where R$_{37}$ can be hydrogen, an alkyl or branched alkyl radical of 1 to 10 carbon atoms, a cycloalkyl radical comprising 3 to 10 carbon atoms, a protecting group as described in Greene et al., phenyl, optionally substituted phenyl, phenylmethyl or optionally substituted phenylmethyl;

R$_{12}$ can be defined as hydrogen; an alkyl or branched alkyl radical comprising 1 to 10 carbon atoms, a cycloalkyl radical of 3 to 10 carbon atoms, or an acyl radical of the type

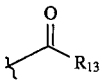

where

R$_{13}$ is as defined above;

R$_1$ and R$_4$ can also be defined as an aryl or heteroaryl radical of the type

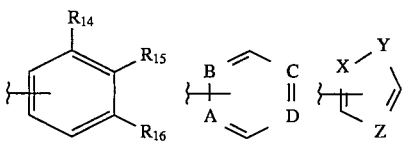

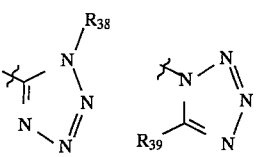

where

R$_{14}$, R$_{15}$, R$_{16}$, A, B, C, D, X, Y, and Z are as defined above;

R$_{38}$ can be defined as hydrogen, an alkyl or branched alkyl radical comprising 1 to 10 carbon atoms, or a cycloalkyl radical comprising 3 to 10 carbon atoms; a protecting group as described in Greene et al.; phenyl, optionally substituted phenyl, phenylmethyl, optionally substituted phenylmethyl, triphenylmethyl; and R$_{39}$ is defined as hydrogen, methyl, phenyl, optionally substituted phenyl, an alkyl or branched alkyl radical comprising 1 to 10 carbon atoms, or a cycloalkyl radical comprising 3 to 10 carbon atoms.

Also the fragment R$_4$—G$_1$ can be defined as R$_{40}$ where R$_{40}$ is an aryl or heteroaryl radical of the type

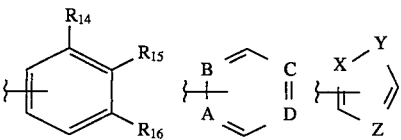

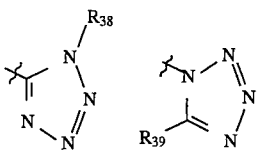

where

R$_{14}$, R$_{15}$, R$_{16}$, A, B, C, D, X, Y, and Z are as defined above; and

R$_{38}$ and R$_{39}$ are defined above;

The fragment R$_1$—G$_2$ can be defined as R$_{41}$ where R$_{41}$ can be defined as an aryl or heteroaryl radical or the type

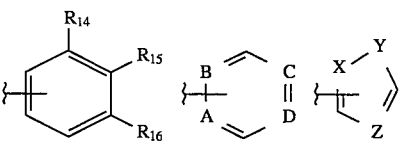

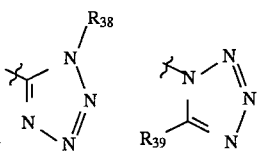

where

R$_{14}$, R$_{15}$, R$_{16}$, A, B, C, D, X, Y, and Z are as defined above; and

R$_{38}$ and R$_{39}$ are defined above; and with the proviso that R$_{40}$ is not equal to R$_{41}$ when R$_{40}$ is equal to;

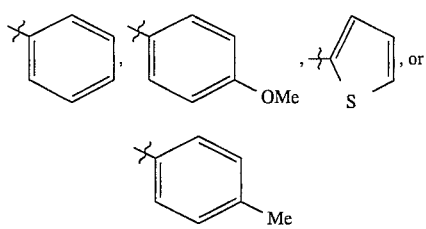

$G_1$ can be nil if $R_1$ is azido, cyano, formyl, halogen, $OR_5$, $SR_6$, $COR_7$, $CO_2R_8$, $NR_9R_{10}$, $CONR_{11}R_{12}$ and $R_{40}$ and $G_2$ is not nil.

The preferred protecting groups for alcoholic functions include, but are not limited to, the following: acetyl, benzoyl, benzyl, tert-butyldimethylsilyl, tert-butyldiphenylsilyl, allyl, methoxyethoxyethyl, triphenylmethyl, tetrahydropyranyl, diphenylmethyl, p-methoxybenzyl, 3,4-dimethoxybenzyl, p-toluenesulfonyl, benzenesulfonyl, tert-butyl, tert-butyloxymethyl, 2-(trimethylsilyl)ethoxymethyl, methoxymethyl, 2-(trimethylsilyl)ethyl, dimethylthexylsilyl, benzyloxymethyl, p-methoxybenzyloxymethyl, (4-methoxyphenoxy)methyl, methylthiomethyl, 2,2,2-trichloroethoxy-methyl, tribenzylsilyl, triphenylsilyl, diphenylmethylsilyl, and tert-butylmethoxyphenylsilyl.

The preferred protecting groups for nitrogen include, but are not limited to, the following: tert-butyloxycarbonyl, benzyloxycarbonyl, 9-phenyl-9-fluorenyl, allyloxycarbonyl, allyl, benzyl, triphenylmethyl, adamantyloxycarbonyl, 2,2,2-trichloroethyloxycarbonyl, 2-(trimethylsilyl)ethoxycarbonyl, p-toluenesulfonyl, benzylidine, diphenylmethyloxycarbonyl, 2-cyanoethyl, 2-cyanoethyloxycarbonyl, 9-fluorenylmethyloxycarbonyl, p-methoxybenzyloxycarbonyl, p-nitrobenzyloxycarbonyl, p-bromobenzyloxycarbonyl, benzenesulfonyl, toluenesulfonyl, p-chlorobenzyloxycarbonyl, o-nitrobenzyloxycarbonyl, benzylidine, N-1,1-dithiomethylene, 2,3,6-trimethyl-4-methoxybenzenesulfonyl, benzylsulfonyl, 2,4,6-trimethoxybenzenesulfonyl, 2,4,6-trimethylbenzenesulfonyl, p-methoxybenzenesulfonyl, and 2-trimethylsilylethanesulfonyl.

The preferred protecting groups for carbonyl oxygen include, but are not limited to, the following: methyl, ethyl, isopropyl, t-butyl, diphenylmethyl, benzyl, 2-cyanoethyl, 2-(trimethylsilyl)ethyl, 2,2,2-trichloroethyl, tert-butyldimethylsilyl, tert-butyldiphenylsilyl, 2-(trimethylsilyl)ethoxymethyl, tribenzylsilyl, triphenylsilyl, diphenylmethylsilyl, tert-butylmethoxyphenylsilyl, p-methoxybenzyl, and phenacyl.

The preferred protecting groups for sulfur include, but are not limited to, the following: triphenylmethyl, tert-butyl, acetyl, benzyl, p-methoxybenzyl, p-nitrobenzyl, diphenylmethyl, 1-adamantyl, 2-cyanoethyl, 2-(4'-pyridyl)ethyl, 2-(phenylsulfonyl)ethyl, 9-fluorenylmethyl, 2-tetrapyranyl, and acetamidomethyl.

The novel process comprises reacting a thiol with a symmetrical or unsymmetrical 1,3-diyne to form a bis(alkylthio)butadiene; eliminating two molecules of a two-carbon fragment from the bis(alkylthio)butadiene to generate a bis(thiyl)butadiene dianion; and oxidizing the two thiyl anions to form 3,6-disubstituted-1,2 dithiin.

The present invention further encompasses the novel compounds capable of being synthesized by the novel process. These compounds include but are not limited to the following dithiin compounds: 3-(acetyloxymethyl)-6-(hydroxymethyl)-1,2 dithiin; 3[(cyclopropylcarbonyloxy)methyl]-6-hydroxymethyl-1,2-dithiin; 3,6-bis[(3'-pyridylcarbonyloxy)methyl]-1,2-dithiin; 3,6-bis[(4-pyridylcarbonyloxy)methyl]-1,2-dithiin; 3-[(4-pyridylcarbonyloxy)methyl]-6-hydroxymethyl-1,2-dithiin; 3,6-bis[(cyclopentanecarbonyloxy)methyl]-1,2-dithiin; 3[(cyclopentanecarbonyloxy)methyl]-6-hydroxymethyl-1,2-dithiin; 3,6-bis[(2'-hydroxybenzoyloxy)methyl]-1,2-dithiin; 3-[(2'-hydroxybenzoyloxy)methyl]-6-hydroxymethyl-1,2-dithiin; 3-[(tert-butyldimethylsilyloxy)methyl]-6-hydroxymethyl-1,2 dithiin; 3-azidomethyl-6-[(tert-butyldimethylsilyloxy)methyl]-1,2 dithiin; 3-azidomethyl-6-hydroxymethyl-1,2 dithiin; 3-[N-(4-methylbenzenasulfonamide)carbonyloxy]-6-(tert-butyldimethylsilyloxymethyl)-1,2 dithiin; 3-[(N-(4-methylbenzene sulfonamide)carbonyl)oxy]-6-(hydroxymethyl)-1,2 dithiin; 3-(Acetamido)methyl-6-[(tert-butyldimethyl-silyloxy)methyl]-1,2-dithiin; 3-(Acetamido)methyl-6-hydroxymethyl-1,2-dithiin; 3-(2'-Hydroxybenzamido)methyl-6-[(tert-butyldimethylsilyloxy)methyl]-1,2-dithiin; 3-(2'-Hydroxybenzamido)methyl-6-hydroxymethyl-1,2-dithiin; 3-Azidomethyl-6-chloromethyl-1,2-Dithiin; 3-[2'-(Tert-butyldimethylsilyloxy)phenyloxy]methyl-6-(tert-butyldimethylsilyloxy)methyl-1,2-Dithiin; 3-[(2'-Hydroxy)phenyloxy]methyl-6-hydroxymethyl-1,2-Dithiin; and 3-[(2'-(Hydroxyphenyl)amino)carbonyloxy]methyl-6-hydroxymethyl-1,2-Dithiin.

Both the novel process for synthesis and the novel disubstituted dithiins are encompassed by the present invention. Also encompassed are pharmaceutical compositions containing the disubstituted dithiins for use as antifungal, antibacterial and antiviral agents.

4. Detailed Description of the Invention

The 1,2-dithiin derivatives described in this invention can be prepared by synthetic methods outlined below. 4.1 Total synthesis of the 1,2-Dithiin Derivatives A novel and versatile synthetic method has been developed to synthesize the symmetrical and unsymmetrical 3,6-disubstituted-1,2-dithiin derivatives of this invention. The process described herein in general starts with a 1,4-disubstituted-1,3-diyne 1. The diyne is allowed to react with 200 to 1000 mole percent of a thiol of the type 2 to give a 1,4-bis(alkylthio)butadiene adduct 3. The reaction temperature for this step is from 0° C. and 50° C. and the reaction mixture is kept under a nitrogen atmosphere for the duration of the reaction. The 1,4-bis(alkylthio)butadiene adduct 3 is dissolved in an anhydrous solvent and treated with 200 to 2000 mole percent of a basic reagent. The reaction is generally performed under a nitrogen atmosphere and at a temperature of −78° C. to +40° C. The reaction mixture is then treated with 50 to 500 mole percent of an oxidizing agent, usually dissolved in an aqueous solution. This step in the process is usually performed at a reaction temperature of −20 C. to +50°C. A liquid-liquid extraction process and chromatographic purification provides the 3,6-disubstituted-1,2-dithiin 4. See Scheme I.

Scheme II provides two alternative embodiments of Scheme I to synthesize the 3,6-disubstituted-1,2 dithiin (e.g. compounds 7 and 10), including a particular route to derivatize a dithiin 7 to a dithiin 10.

As also described in Scheme II, the appropriate 1,4-disubstituted-1,3-diyne 1 can be prepared using established synthetic methods and protecting groups to provide desired unsymmetrical 3,6-disubstituted-1,2-dithiins of general structure 4. This is exemplified in Scheme II wherein the 1,4-disubstituted-1,3-diyne (5) is reacted with tert-butyldimethylsilyl chloride to form a protected diyne (8); the diyne 8 is then reacted with the mercaptan $HSCH_2CH_2CN$ to form 1-hydroxy-6-(t-butyldimethylsilyloxy)-2,5-bis[2'-(cyanoethyl)thio]-2,4-hexadiene (9); the hexadiene 9 is then reacted with a potassium t-butoxide and potassium ferrocyanide to form 3-[(tert-butyldimethylsilyloxy)methy]-6-hydroxymethyl-1,2-dithiin (10) (See Examples 13–15).

With unsymmetrical 3,6-disubstituted-1,2-dithiins, the cyclized product 4 can be converted to other 3,6-disubstituted-1,2-dithiin derivatives using established synthetic methods and protecting groups as outlined in Schemes III to VII. These Schemes demonstrate the versatility of the dithiin product 4.

The above novel synthetic method is preferably conducted in a reaction solvent selected from the group consisting of tetrahydrofuran, diethyl ether, diisopropyl ether, t-butyl methyl ether, t-butyl ethyl ether, ethylene glycol, ethylene glycol methyl ether, diethylene glycol methyl ether, dichloromethane, dichloroethane, dimethylformamide, methanol, ethanol, benzene, toluene, dimethylacetamide, dimethylsulfoxide, N-methylpyrrolidinone, water, and mixtures thereof; and where the reaction temperature for the reaction of the thiol with the diyne is $-20°$ to $80°$ C. or $0°$ C. to $50°$ C.

The preferred basic reagent for the novel synthetic method is selected from the group consisting of sodium amide, potassium amide, lithium amide, sodium hydride, n-butyllithium, s-butyllithium, phenyllithium, triphenylmethyllithium, t-butyllithium, potassium t-butoxide, sodium t-butoxide, sodium methoxide, sodium s-butoxide, lithium diisopropylamide, sodium diisopropylamide, potassium diisopropylamide, sodium bis(trimethylsilyl)amide, potassium bis(trimethylsilyl)amide, lithium bis(trimethylsilyl)amide, lithium isopropylcyclohexylamide, potassium isopropylcyclohexylamide, sodium isopropylcyclohexylamide, 1,8-diazabicyclo[5.4.0]undec-7-ene (DBU), 1,5-diazabicyclo[4.3.0]non-5-ene (DBN), 1,4-diazabicyclo[2.2.21]octane (Dabco), potassium carbonate, sodium carbonate and mixtures thereof.

The preferred oxidizing agent for the novel synthetic method is selected from the group consisting of bromine, chlorine, iodine, osmium tetroxide, potassium permanganate, peracetic acid, trifluoroperacetic acid, m-chloroperbenzoic acid, N-bromosuccinimide, N-chlorosuccinimide, N-iodosuccinimide, sodium periodate, potassium periodate, potassium peroxymonosulfate (OXONE), potassium dichromate, pyridinium chlorochromate, pyridinium dichromate, potassium ferrocyanide, potassium ferrocyanide trihydrate, potassium superoxide, hydrogen peroxide, bis(trimethysilyl)peroxide, lead tetraacetate, lithium perchlorate, lithium peroxide, manganese dioxide, nickel(II) oxide, nickel peroxide, potassium chromate, sodium nitrate, potassium nitrate, nitric acid, silver(I) oxide, silver(II) oxide, sodium percarbonate, sodium perchlorate, lithium perchlorate, sodium peroxide, tetrabutylammonium chlorochromate, tetrabutylammonium periodate and benzoyl peroxide.

Scheme I
General Scheme for the Synthesis of Unsymmetrical
3,6-Disubstituted-1,2-Dithiins

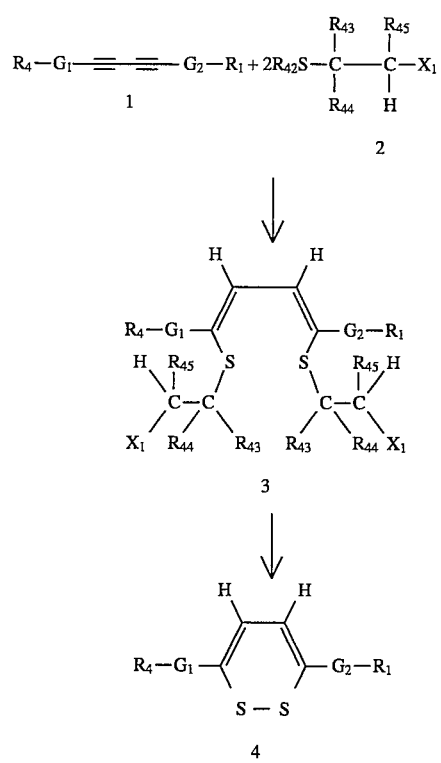

$R_1$, $R_4$, $G_1$, and $G_2$ are as defined in Section 3.
$X_1$ = CHO, CN, $NO_2$, $S(O)_mR_{54}$, $P(O)(OR_{57})_2$, $CONR_{58}R_{59}$, $CO_2R_{60}$, $p-O_2NC_6H_4$, $R_{43}$, $R_{44}$, and $R_{45}$ can be independently hydrogen, an alkyl or branched alkyl radical comprising 1 to 10 carbon atoms, a cycloalkyl radical of 3 to 10 carbon atoms, or an aryl or heteroaryl substituent of the type

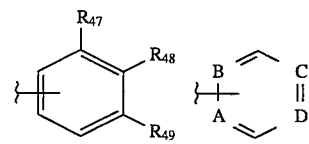

wherein $R_{47}$, $R_{48}$ and $R_{49}$ can be independently hydrogen, a halogen, nitro, cyano, trifluoromethyl, an alkyl or branched alkyl radical comprising 1 to 10 carbon atoms, a cycloalkyl radical of 3 to 10 carbon atoms, $CO_2R_{50}$, or $CONR_{51}R_{52}$, where $R_{50}$ is hydrogen, methyl, ethyl, 1-(methyl)ethyl, n-propyl, an alkyl or branched alkyl radical comprising 1 to 10 carbons, or a cycloalkyl radical of 3 to 20 carbon atoms, phenyl, optionally substituted phenyl, or a protecting group;

$R_{51}$ and $R_{52}$ can be the same or different, or be part of a ring comprising 2 to 10 carbon atoms, $R_{51}$ can be hydrogen, alkyl, branched alkyl, or a cycloalkyl radical of 1 to 10 carbon atoms, phenyl, optionally substituted phenyl, or a protecting group;

$R_{52}$ can be hydrogen, an alkyl or branched alkyl radical comprising 1 to 10 carbon atoms, a cycloalkyl radical of 3 to 10 carbon atoms, phenyl, optionally substituted phenyl; and A, B, C and D can be independently N, CH or $NR_{53}$, where $R_{53}$ is methyl, ethyl, 1-(methyl)ethyl, n-propyl, or an alkyl or branched alkyl radical comprising 1 to 10 carbon atoms, or a cycloalkyl radical of 3 to 20 carbon atoms;

$X_1$ can be cyano, nitro, CHO, $S(O)_m R_{54}$, $P(=O)(OR_{57})_2$, $CO_2R_{58}$, $CONR_{59}R_{60}$, where m is an integer from 1 to 2;

$R_{54}$ is an alkyl or branched alkyl radical comprising 1 to 10 carbon atoms, a cycloalkyl radical of 3 to 20 carbon atoms, phenyl or optionally substituted phenyl, or an aryl or heteroaryl ring of the type

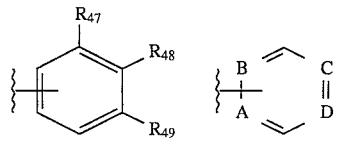

where $R_{47}$, $R_{48}$, $R_{49}$, A, B, C, and D are as defined above;

$R_{54}$ can also be $NR_{55}R_{56}$, where $R_{55}$ and $R_{56}$ can be the same or different, or be part of a ring comprising 2 to 10 carbon atoms; $R_{55}$ can be hydrogen, an alkyl or branched alkyl radical comprising 1 to 10 carbon atoms, a cycloalkyl radical comprising 3 to 10 carbon atoms, phenyl, optionally substituted phenyl, or a protecting group;

$R_{56}$ can be hydrogen, an alkyl or branched alkyl radical comprising 1 to 10 carbon atoms, a cycloalkyl radical of 3 to 10 carbon atoms, phenyl, optionally substituted phenyl, $R_{57}$ can be hydrogen, methyl, ethyl, 1-(methyl)ethyl, n-propyl, an alkyl or branched alkyl radical comprising 1 to 10 carbon atoms, a cycloalkyl radical of 3 to 20 carbon atoms, phenyl, optionally substituted phenyl, or a protecting group;

$R_{58}$ can be hydrogen, methyl, ethyl, 1-(methyl)ethyl, n-propyl; an alkyl or branched alkyl radical comprising 1 to 10 carbon atoms, a cycloalkyl radical of 3 to 20 carbon atoms or a protecting group;

$R_{59}$ and $R_{60}$ can be the same or different, or be part of a ring comprising 2 to 10 carbon atoms, $R_{59}$ can be hydrogen, an alkyl or branched alkyl radical comprising 1 to 10 carbon atoms, a cycloalkyl radical comprising 3 to 10 carbon atoms, phenyl, optionally substituted phenyl, or a protecting group;

$R_{60}$ can be hydrogen, an alkyl or branched alkyl radical comprising 1 to 10 carbon atoms, a cycloalkylradical of 3 to 10 carbon atoms, phenyl, or optionally substituted phenyl; and $NR_{59}R_{60}$ can also be defined as a radical of the type

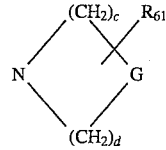

where c is an integer from 0 to 10;

d is an integer from 1 to 10;

$R_{61}$ is an alkyl, branched alkyl, or a cycloalkyl radical comprising 1 to 10 carbon atoms; an aryl or heteroaryl radical of the type

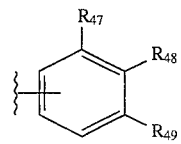

where $R_{47}$, $R_{48}$, and $R_{49}$ are as defined above;

$R_{61}$ can also be $OR_{62}$, $SR_{63}$ or $NR_{64}R_{65}$ where $R_{62}$ is defined as hydrogen; an alkyl or branched alkyl radical comprising 1 to 10 carbon atoms, a cycloalkyl radical of 3 to 10 carbon atoms, a protecting group, or an acyl radical of the type

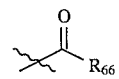

where $R_{66}$ is methyl, ethyl, cyclopropyl, propyl, 1-(methyl)ethyl, cyclobutyl, cyclopentyl; an alkyl or branched alkyl radical comprising 1 to 10 carbon atoms, a cycloalkyl radical of 3 to 20 carbon atoms, or an aryl or heteroaryl ring of the type

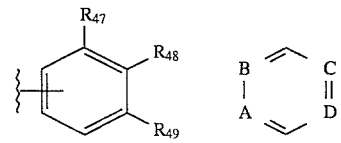

where $R_{47}$, $R_{48}$, and $R_{49}$, A, B, C, and D are as defined above;

$R_{63}$ is defined as hydrogen, an alkyl or branched alkyl radical comprising 1 to 10 carbon atoms, a cycloalkyl radical of 3 to 10 carbon atoms, a protecting group, or an acyl radical of the type

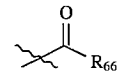

where $R_{66}$ is as defined above;

$R_{64}$ and $R_{65}$ can be independently hydrogen, an alkyl or branched alkyl radical comprising 1 to 10 carbon atoms, a cycloalkyl radical of 1 to 10 carbon atoms, or a protecting group;

G is $-CH_2-$, oxygen, a heteroatom of the type $S(O)_e$, or $NR_{67}$, where e is an integer from 0 to 2; and $R_{67}$ is defined as hydrogen; an alkyl or branched alkyl radical comprising 1 to 10 carbon atoms, a cycloalkyl radical comprising 3 to 10 carbon atoms, a protecting group, or an acyl radical of the type

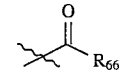

where
$R_{66}$ is as defined above; and
alternatively, the fragment $HCR_{45}X_1$ can be defined as
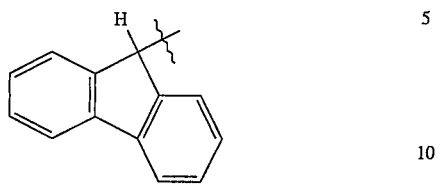
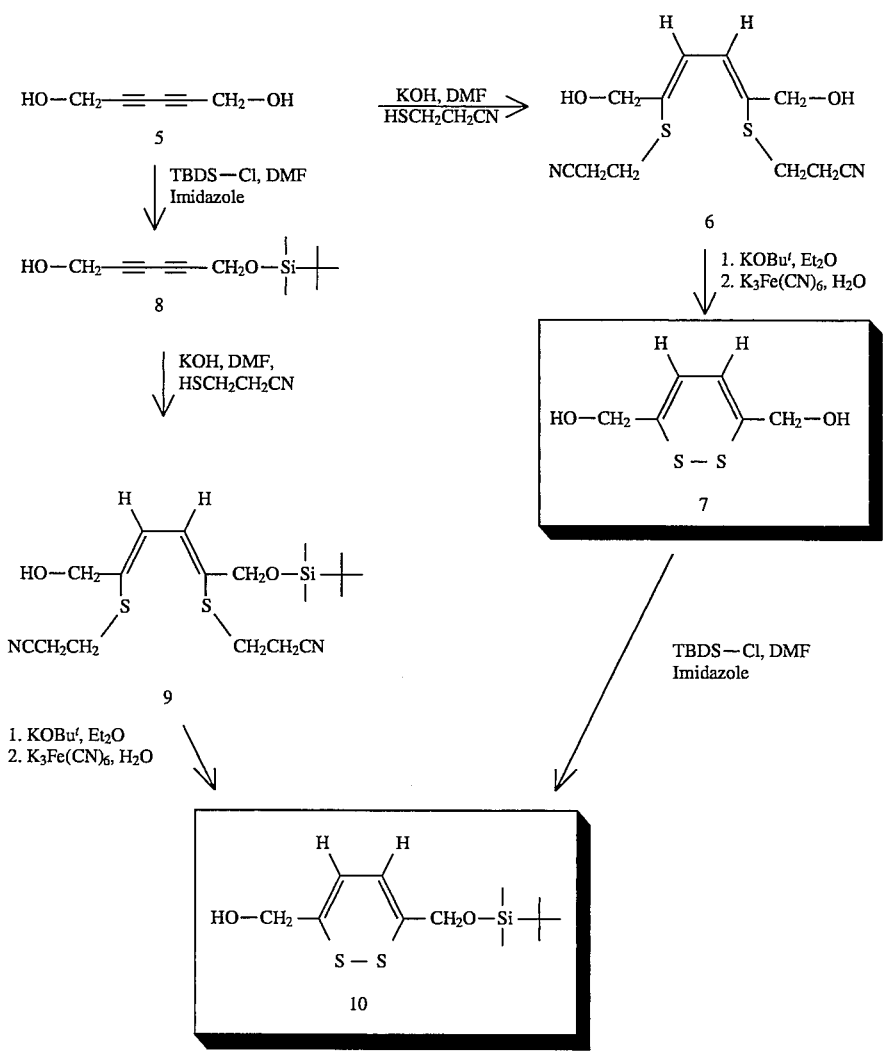
Scheme II
Synthesis of Symmetrical and Unsymmetrical
3,6-Disubstituted-1,2-Dithiins Using the Novel and Versatile
Methodology Scheme III
Synthesis of Mono- and Bis(acyl)-1,2-Dithiins
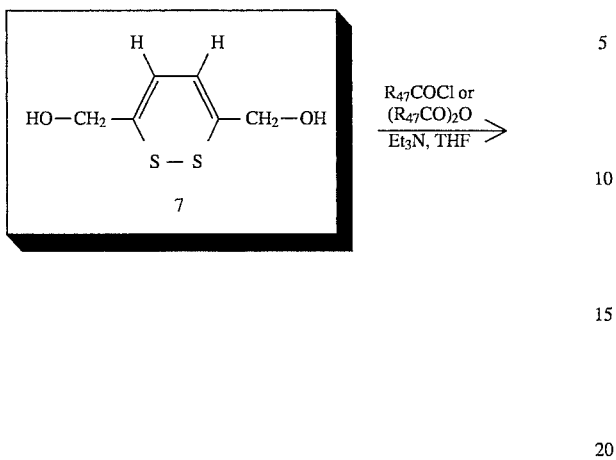
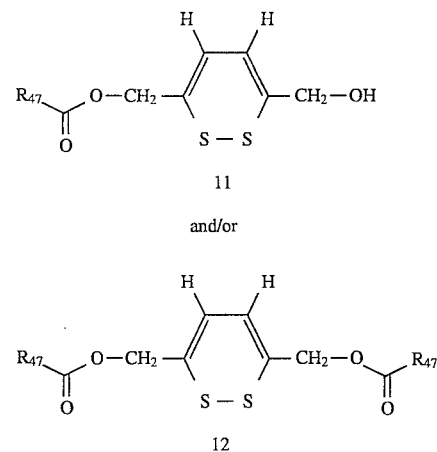
$R_{47}$ = methyl, cyclopropyl, cyclopentyl, 3-pyridyl, 4-pyridyl, 2-hydroxyphenyl

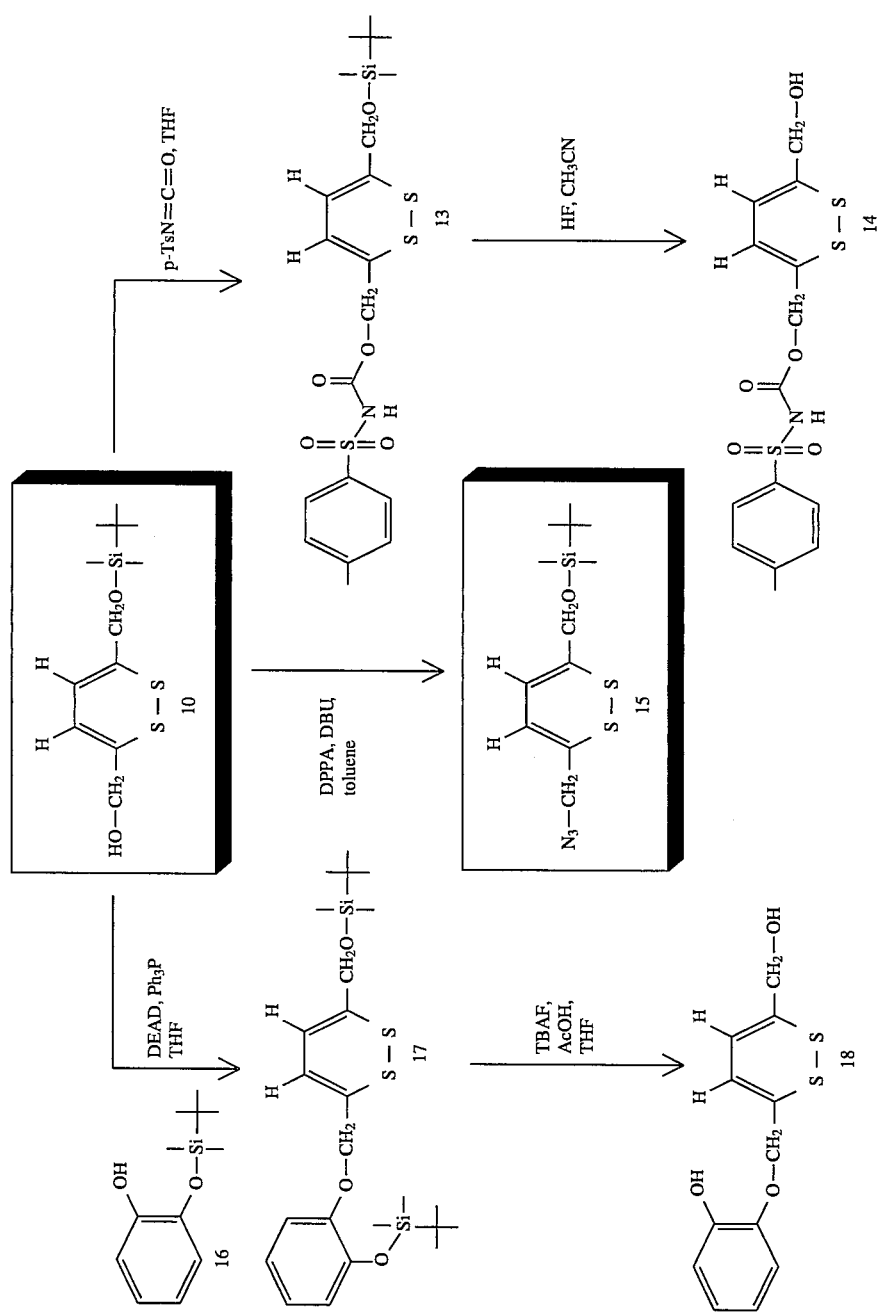

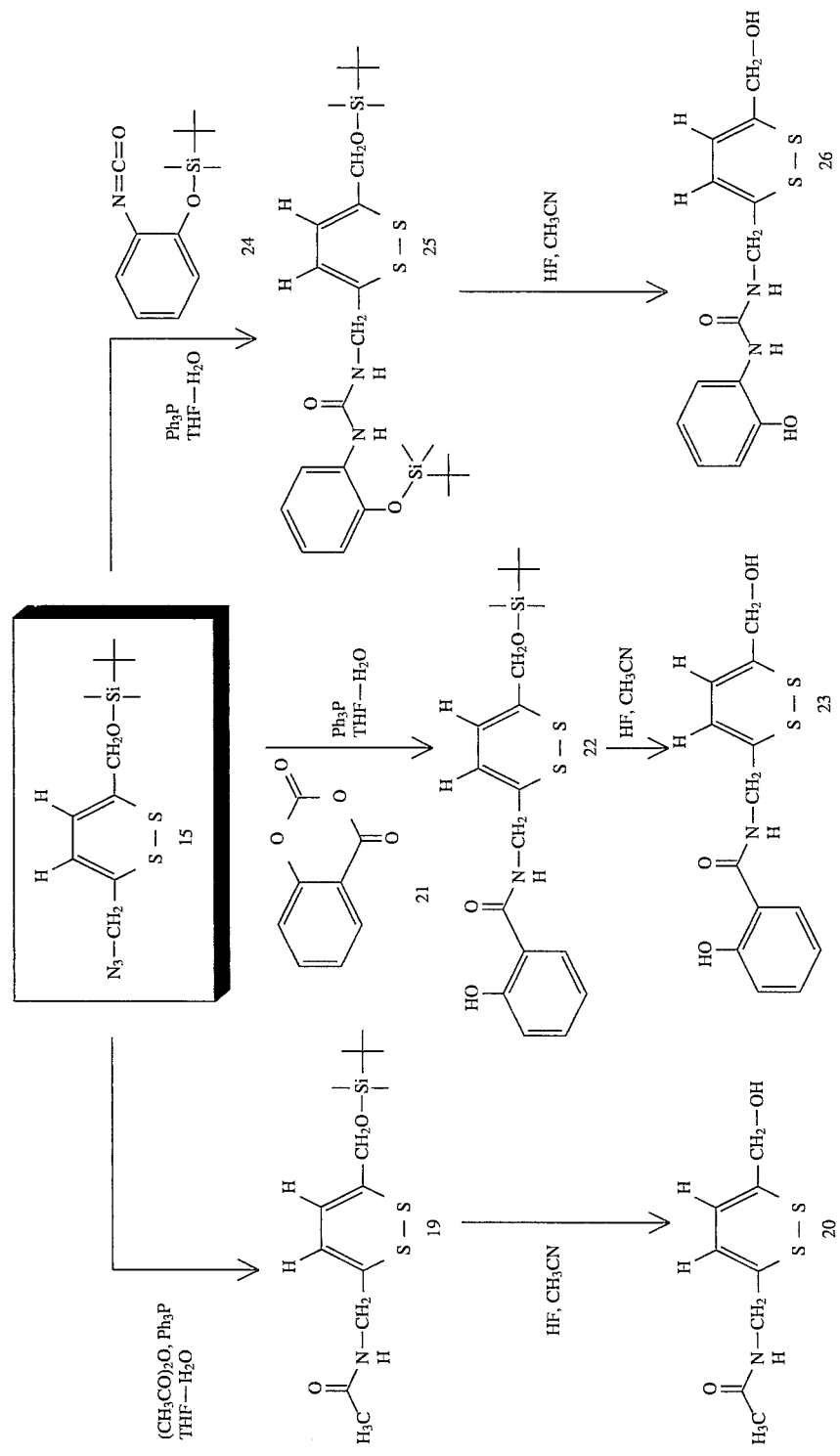

Scheme VI
Functionalization of the Versatile Azide Intermediate (Continued)

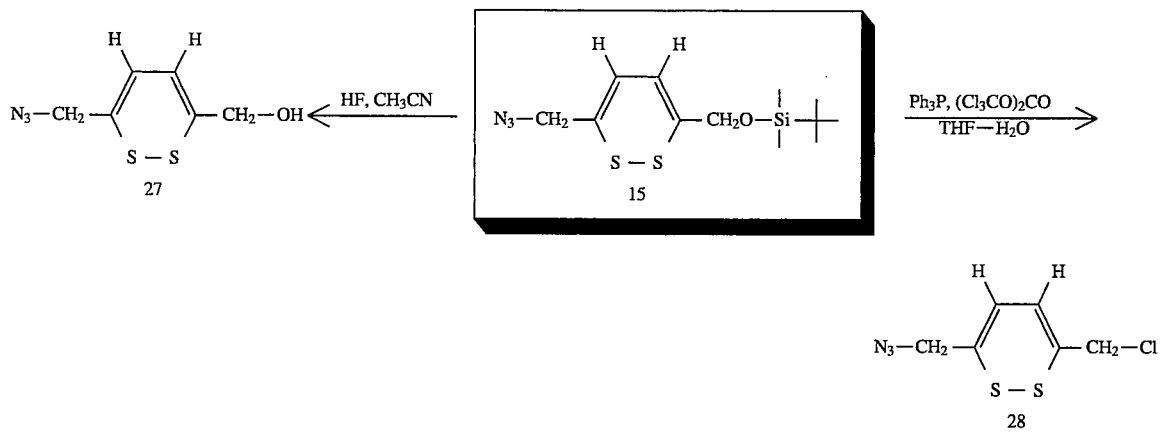

Scheme VII
Synthesis of Carbamates From Versatile Intermediate 10

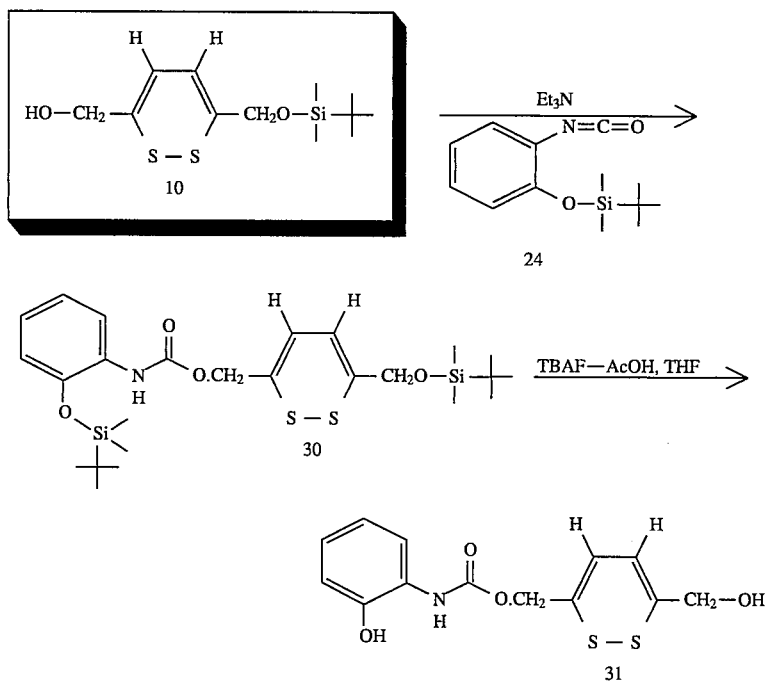

4.2 Novel Compounds

The novel compounds capable of being synthesized by the novel process include but are not limited to the following dithiin compounds: 3-(acetyloxymethyl)-6-(hydroxymethyl)-1,2 dithiin; 3[(cyclopropyl carbonyloxy)methyl]-6-hydroxymethyl-1,2-dithiin; 3,6-bis[(3'-pyridylcarbonyloxy)methyl]-1,2-dithiin; 3,6-bis[(4-pyridylcarbonyloxy)methyl]-1,2-dithiin; 3-[(4-pyridylcarbonyloxy)methyl]-6-hydroxymethyl-1,2-dithiin; 3,6-bis[(cyclopentane carbonyloxy)methyl]-1,2-dithiin; 3-[(cyclopentane carbonyloxy)methyl]-6-hydroxymethyl-1,2-dithiin; 3,6-bis[(2'-hydroxybenzoyloxy)methyl]-1,2-dithiin; 3-[(2'-hydroxybenzoyloxy)methyl]-6-hydroxymethyl-1,2-dithiin; 3-[(tert-butyldimethylsilyloxy) methyl]-6-hydroxymethyl-1,2-dithiin; 3-azidomethyl-6-[(tert-butyldimethylsilyloxy)methyl]-1,2-dithiin; 3-azidomethyl-6-hydroxymethyl-1,2-dithiin; 3-[N-(4-methylbenzenasulfonamide)carbonyloxy]-6-(tert-butyldimethylsilyloxymethyl)-1,2 dithiin; 3-[(N-(4methylbenzene sulfonamide) carbonyl)oxy]-6-(hydroxymethyl)-1,2 dithiin; 3-(Acetamido)methyl-6-[(tert-butyldimethyl-silyloxy)methyl]-1,2-dithiin; 3-(Acetamido)methyl-6-hydroxymethyl-1,2-dithiin; 3-(2'-Hydroxybenzamido)methyl-6-[(tert-butyldimethylsilyloxy)methyl]-1,2-dithiin; 3-(2'-Hydroxybenzamido)methyl-6-hydroxymethyl-1,2-dithiin; 3-Azidomethyl-6-chloromethyl-1,2-Dithiin; 3-[2'-(Tert-butyldimethylsilyloxy)phenyloxy]methyl-6-(tert-butyldimethylsilyloxy)methyl-1,2-Dithiin; 3-[(2'-Hydroxy)phenyloxy]methyl-6-hydroxymethyl-1,2-Dithiin; and 3-[(2'-(Hydroxyphenyl)amino)carbonyloxy]methyl-6-hydroxymethyl-1,2-Dithiin.

4.3 Methods of Use

The dithiin derivatives described in this invention are all useful in treating fungal infections including but not limited to *Candida albicans, Cryptococcus neoformans, Aspergillus fumigatus, Candida krusei, Candida parapsilosis, Candida tropicalis* and *Trichophyton rubrum* by the administration to a warm-blooded animal of a therapeutically effective amount of a dithiin derivative. The pharmaceutical composition comprising the dithiin derivative or its pharmaceutically acceptable salt used for such administration may also contain pharmaceutically acceptable excipients and carriers, acceptable in the sense of compatible with other ingredients and not deleterious to the recipient thereof.

In order to treat a fungal infection, the antifungal agents described in this invention may be administered to a warm-blooded animal intravenously, intraperitoneally, subcutaneously, intramuscularly, orally, topically, by aerosol, or combinations thereof.

In general, the pharmaceutical compositions or formulations are prepared by uniformly and intimately bringing into association the active ingredient with a liquid carrier or finely divided solid carrier or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered an a pharmaceutically acceptable carrier. A preferred topical delivery system is a transdermal patch containing the ingredient to be administered.

Formulations suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients particularly mentioned above the formulations of this invention may include other agents conventional in the art having regard to the type of formulation in question, for example, those suitable for oral administration may include flavoring agents.

The antifungal agent of the dithiin derivatives described herein can be administered intravenously in a range of about 0.1 to about 400 mg/kg body weight, preferably about 0.1 to about 10 mg/kg body weight.

The antifungal agent of the dithiin derivatives described herein can be administered intraperitoneally in a range of about 0.1 to about 400 mg/kg body weight, preferably about 0.1 to about 10 mg/kg body weight.

The antifungal agent of the dithiin derivatives described herein can be administered subcutaneously in a range of about 1 to about 400 mg/kg body weight, preferably about 1.0 to about 20 mg/kg body weight.

The antifungal agent of the dithiin derivatives described herein can be administered intramuscularly in a range of about 1 to about 400 mg/kg body weight, preferably about 1.0 to about 20 mg/kg body weight.

The antifungal agent of the dithiin derivatives described herein can be administered orally in a range of about 1.0 to about 400 mg/kg body weight, preferably about 5.0 to about 30 mg/kg body weight.

The antifungal agent of the dithiin derivatives described herein can be administered topically including to skin, ocular and oral tissues in a range of about 1.0 to about 15% by weight of the formulation, preferably about 5.0 to about 15% by weight of the formulation.

The antifungal agent of the dithiin derivatives described herein can be administered by aerosol in a range of about 5.0 to about 400 mg/kg body weight, preferably about 5.0 to about 30 mg/kg of body weight/day.

The dithiin derivatives described in this invention are also useful as an active agent in a disinfectant or cleaning composition, which composition possesses fungicidal and/or fungistatic, antibacterial and/or antiviral properties.

5. EXAMPLES

The present invention may be more fully understood from the following examples, which are given by way of illustration and not by way of limitation.

5.1 General Experimental Section.

Tetrahydrofuran (THF) was distilled from potassium/benzophenone; benzene, triethylamine, and methylene chloride were distilled from calcium hydride. Anhydrous dimethylformamide (DMF) was obtained from Aldrich. 4H-1,3-benzodioxin-2,4-dione was prepared according to the literature (F. A. Dean, K. B. Hindley, and S. Small, *J. Chem. Soc., Perkin Trans. 1* 1972, 2007). Flash column chromatography was performed on Whatman 230–400 mesh silica gel using nitrogen pressure. $^1$H and $^{13}$C NMR were provided by the Shaman Pharmaceutical Physical Chemistry Department using a Varian 400 MHz spectrometer with chloroform as an internal reference unless otherwise noted. NMR shifts were expressed in ppm downfield from internal tetramethylsilane. NMR assignments were determined on the basis of COSY, HMQC, HMBC and DEPT experiments performed on selected intermediates. NMR coupling constants are reported in Hertz. Mass spectrometry was performed by the Physical Chemistry Department at Shaman Pharmaceuticals, or by the Analytical Services Department and the University of California, Berkeley. Elemental analyses were performed by Analytical Services Department at the University of Calif., Berkeley. Melting points were determined using a Buchi model 535 melting point apparatus and are uncorrected.

5.2 Examples

Example 1

2-(Cyanoethyl)mercaptan. 3-Chloropropionitrile (500 g; 5.58 mol) was combined with thiourea (575 g; 7.57 mol) and 375 mL of water and refluxed for 2 h in 120° C. bath. After cooling the solution to room temperature, 600 mL of cold acetone was added. The light yellow crystalline isothiouronium salt precipitated immediately and was collected by filtration after standing for 15 minutes at 5°–6° C. The solid was washed with 7 L of cold acetone and twice with diethyl ether (2×1.5 L), then air dried for 2 days to give 750 g (81%) of thiouronium salt. $^1$H NMR (D$_2$O) δ3.56 (t, 2H), 3.105 (t, 2H); $^{13}$C NMR (D$_2$O; 3 of 4 expected signals observed) δ118.730, 26.182, 17.952.

The above salt was divided into 360 g and 390 g portions and dissolved in 514 mL and 560 mL of water, respectively. To each of these solutions was added 240 mL and 260 mL of 50% NaOH respectively, and the reaction mixtures were stirring under nitrogen for 30 min at 45°–50° C. in the flask. The mixtures were quickly cooled to room temperature with an water-ice bath, then 400 mL of ether was added to each flask and both mixtures were stirred for 5 minutes. Each reaction mixture was washed twice by 400 mL of diethyl ether then the aqueous layer was brought to pH 7 by the addition of 6N H$_2$SO$_4$ and extracted with 3×450 mL of ether (each reaction), for both reactions were used 5.5 L of ether. The combined ether extracts were dried (MgSO$_4$) and the solvent was removed by rotary evaporation to give 230 g (58 %) of crude 2-(cyanoethyl)mercaptan. This material was vacuum distilled (b.p. 42°–43° C., 6 mm) to afford 145 g (37%) of the title mercaptan as a colorless liquid: $^1$H NMR (CDCl$_3$) δ2.75–2.68 (m, 2H, CH$_2$), 2.65–2.60 (m, 2H, CH$_2$), 1.770 (t, J=8.8 Hz, 1H, SH); $^{13}$C NMR (CDCl$_3$) δ117.835, 22.314, 20.083.

Example 2

1,6-Dihydroxy-2,4-Bis[2'-(cyanoethyl)thio]-2,5-Hexadiene (6)

To a stirred solution of KOH (1.27 g; 22.6 mmol) in 4 mL of water was added the DMF (50 mL) followed by the mercaptan HSCH$_2$CH$_2$CN (19.75 g, 500 mol %). The resulting clear solution was stirred under nitrogen by room temp. for 20 minutes, then 5.00 g (45.0 mmol) of 1,6-dihydroxy-2,4-hexadiene (5) was added. After 3 minutes following the addition of the diyne, the flask became slightly warm and the reaction mixture had become orange. The reaction mixture was diluted with 100 mL of water and 50 mL of saturated sodium chloride. The solution was extracted with three 150-mL portions of ethyl acetate and the combined organic phases were washed with 100 mL of saturated aqueous sodium chloride. The organic phase was dried (MgSO$_4$) and concentrated in vacuo. The residue was chromatographed over silica gel (ethyl acetate-hexane, 1:1; then ethyl acetate) to give 7.89 g (61.2%) of the desired bis(mercaptan) adduct 6. $^1$H NMR (CD$_3$OD) δ7.214 (s, 2H), 4.298 (s, 4H), 3.062 (t, J=6.8 Hz, 4H, CH$_2$S), 2.74.7 (t, J=6.4 Hz, 4H, CH$_2$CN); $^{13}$C NMR (CD$_3$OD) δ138.7, 130.4, 119.8, 66.7, 28.7, 19.5.

Example 3

3,6-Bis(hydroxymethyl)-1,2-Dithiin (7)

To a stirred solution of the product from Example 2 (1.00 g; 3.52 mmol) in 100 mL of dry diethyl ether was added 3.95 g (35.2 mmol) of solid potassium t-butoxide. The resulting suspension was stirred for 5 minutes then 70 mL of water was added. The reaction mixture was treated with a solution of potassium ferrocyanide (2.55 g; 7.74 mmol) in 30 mL of water. The reaction mixture was extracted with diethyl ether (5×100 mL), dried (Na$_2$SO$_4$) and concentrated in vacuo. The residue was chromatographed over silica gel (ethyl acetate-hexane, 1:1) to give 204 mg (33%) of the dithiin. $^1$H-NMR (CDCl$_3$) δ6.41 (s, 2H, C=CH), 4.30 (d, J=6 Hz, 4H, CH$_2$O), 1.79 (t, J=6 Hz, 2H, OH); $^{13}$C-NMR (CDCl$_3$) δ134.895 (s), 125.147 (d), 64.612 (t).

Example 4

3-(Acetyloxymethyl)-6-(hydroxymethyl)-1,2-Dithiin

To a solution of 150 μL (160 mg; 110 mol %) of acetic anhydride and 20 mL of anhydrous pyridine, cooled to 0° C. with an ice-sodium chloride bath, was added 250 mg (1.42 mmol) of dithiin. The reaction mixture was stirred at 0° C. for several hours. TLC showed a big amount of starting material. The reaction mixture was warmed to 10° C. for 2 hours and then it was stored in a cold room overnight. The reaction mixture was poured into a mixture of ice-cold 1M aqueous H$_3$PO$_4$ (200 mL) and Et$_2$O (200 mL). The organic layer was washed with saturated NaHCO$_3$ (250 mL), washed with H$_2$O (100 mL), dried (Na$_2$SO$_4$) and evaporated to a orange oil which was purified silica gel chromatography (ethyl acetate-hexane, 1:3) to give 100 mg (32.3%) of the monoacetate. $^1$H NMR (CDCl$_3$) δ6.396 (s, 2H), 4.714 (s, 2H), 4.290 (d, 2H, J=4.80), 2.121 (s, 3H), 1.637 (s, 1H); $^{13}$C NMR (CDCl$_3$) δ170.481, 136.208, 128.121, 129.183, 128.114, 124.821, 65.401, 64.491; MS (EI) m/z=128.0 (100%), 218 (M$^+$).

Example 5

3,6-Bis[(cyclopropylcarbonyloxy)methyl]-1,2-Dithiin and 3-[(cyclopropylcarbonyloxy)methyl]-6-hydroxymethyl-1,2-Dithiin To a stirred solution of 2.02 g (11.5 mmol) of the dithiin in 100 mL of dry tetrahydrofuran, previously cooled for 10 minutes in an ice-salt bath (internal temperature: −7° C.), was added 2.0 mL (1.45 g; 14.3 mmol) of triethylamine, followed by 1.0 mL (1.15 g; 11.0 mmol) of cyclopropanecarbonyl chloride. Only a 2° C. rise in the internal temperature was noted after the addition of both reagents. After 2.5 h, TLC analysis showed the presence of two less-polar products along with starting material. The reaction mixture was allowed to warm up to room temperature overnight then it was poured into a vigorously stirred, cold mixture of 100 mL of diethyl ether and 50 mL of 1M aqueous phosphoric acid. The layers were separated and the aqueous phase was extracted with two 100-mL portions of diethyl ether and the combined organic phases were washed with 100 mL of 10% aqueous sodium bicarbonate, followed by two 50-mL portions of saturated aqueous sodium chloride. The organic phase was dried ($MgSO_4$) and concentrated in vacuo to give 2.85 g of a red-orange oil. This product was purified by chromatography over 150 g of silica gel (ethyl acetate-hexane, 1:3 then ethyl acetate-hexane, 1:1) give 1.17 g (33%) of the bis(cyclopropylcarbonyl)dithiin as a reddish-yellow oil: $^1$H-NMR ($CDCl_3$) δ6.38 (s, 2H, C=CH), 4.71 (s, 4H, $CH_2O$), 1.700–1.625 (m, 2H, CHCO), 1.050–1.010 (m, 2H, $CH_2$), 0.944–0.880 (m, 2H, $CH_2$); $^{13}$C-NMR ($CDCl_3$) δ174.273, 130.571, 127.582, 65.212, 12.771, 8.864.

Continued elution afforded 1.16 g (41%) of the monocyclopropyl ester as a reddish-orange solid. $^1$H-NMR ($CDCl_3$) δ6.39 (s, 2H, C=CH), 4.72 (s, 2H, $CH_2O$) 4.28 (d, J=6 Hz, 2H, $CH_2O$), 1.984 (t, J=6 Hz, 1H, OH) 1.695–1.635 (m, 1H, CHCO), 1.060–1.020 (m, 2H, $CH_2$), 0.930–0.880 (m, 2H, $CH_2$); $^{13}$C-NMR ($CDCl_3$) δ 174.410, 136.109, 129.342, 127.924, 124.844, 65.401, 64.499, 12.801, 8.856.

Lastly, 358 mg (18%) of starting diol was recovered.

Example 6

3,6-Bis[(3'-pyridylcarbonyloxy)methyl]-1,2-Dithiin

To a heterogenous mixture of nicotinoyl chloride hydrochloride (303 mg; 1.70 mmol) in THF (7.5 mL) was injected 750 μL (0.545 mg; 5.38 mmol) of $Et_3N$ to give a cloudy solution. Next, dithiin diol (30 mg; 0.17 mmol) was added. The bath temperature was kept at −35° C. to −40° C. with a dry ice/$CH_3CN$ bath and the reaction mixture was stirred for 3 hours after which time TLC showed that the starting material had been consumed. The reaction mixture was partitioned between $CH_2Cl_2$ (80 mL) and 1M aqueous $H_3PO_4$ (80 mL). The water layer was extracted with $CH_2Cl_2$ (2×40 mL) and the combined $CH_2Cl_2$ extracts were washed by $NaHCO_3$ (10% aqueous solution) then with water (40 mL). The organic phase was dried ($Na_2SO_4$) and concentrated in vacuo. The crude material was chromatographed on silica gel (ethyl acetate-hexane, 1:1, then ethyl acetate) to give 30 mg (38 %) of the diester. $^1$H NMR ($CDCl_3$) δ9.263 (br s, 2H, ArH) 8.812 (dd, J=5.2, 2.0 Hz, 2H, ArH), 8.323 (br d, J=7.6 Hz, 2H, ArH), 7.424 (dd, J=7.6, 4.8 Hz, 2H, ArH), 6.521 (s, 2H, C=CH), 5.014 (s, 4H, $CH_2O$); $^{13}$C NMR ($CDCl_3$) δ153.822, 151.030, 137.247, 123.410, 66.357, 36.977.

Example 7

3,6-Bis[(4-pyridylcarbonyloxy)methyl]-1,2-Dithiin

To a heterogeneous mixture of isonicotinoyl chloride hydrochloride (202 mg, 1.13 mmol) in THF (5 mL) was added triethylamine (500 μL; 363 mg, 3.59 mmol) and then 20 mg (0.113 mmol) of 3,6-bis(hydroxymethyl)-1,2-dithiin. After 8 hours, the reaction was complete by thin-layer chromatography. The reaction mixture was partitioned between 1M aqueous $H_3PO_4$ (50 mL) and $CH_2Cl_2$ (80 mL). The layers were separated and the organic phase was washed with 10% aqueous solution of sodium bicarbonate and water, then dried ($Na_2SO_4$). The organic phase was concentrated in vacuo and the residue was purified by chromatography on silica gel (ethyl ether) to give 27 mg (62.8%) of the bis(isonicotinyl)ester. $^1$H NMR ($CDCl_3$) δ8.82 (d, J=4.8 Hz, 4H), 7.88 (d, J=4.4 Hz, 4H), 6.52 (s, 2H), 5.02 (s, 4H); $^{13}$C NMR ($CDCl_3$) δ64.533, 150.75, 130.329, 128.341, 122.894, 66.251, 29.687.

Example 8

3-[(4-pyridylcarbonyloxy)methyl]-6-hydroxymethyl-1,2-Dithiin

To a solution of isonicotinoyl chloride hydrochloride (202 mg; 1.13 mmol) in THF (5 mL) was added triethylamine (500 μL; 363 mg, 3.59 mmol). The mixture was cooled to −45° C. using a dry ice/$CH_3CN$ bath, then 20 mg (0.113 mmol) dithiin diol was added and the reaction mixture was kept at a temperature of −45° C. for 7 h at which time TLC analysis showed that the reaction was complete. Then 50 mL of a 1M solution of $H_3PO_4$ was added and the reaction mixture was extracted with $CH_2Cl_2$ (3×50 mL), washed with 5% aqueous solution of sodium bicarbonate, water, then dried over $Na_2SO_4$. The organic layer was evaporated and purified by silica gel chromatography (ethyl ether-hexane, 1:1) to give 13 mg (29.6%) of diester, identical to material prepared previously.

Continued elution afforded 66 mg (18.8%) of mono(i-sonicotinoyl)ester. $^1$H NMR ($CDCl_3$) δ8.80 (d, J= 5.2 Hz, 2H), 7.87 (d, J=5.2 Hz, 2H), 6.46 (dd, J=4.0, 6.0 Hz, 2H), 5.00 (s, 2H), 4.31 (s, 2H); $^{13}$C NMR ($CDCl_3$;9 of 10 expected signals observed) δ164.571, 150.689, 128.849, 128.280, 124.685, 122.917, 66.547, 64.445, 29.679.

Example 9

3,6-Bis[(cyclopentanecarbonyloxy)methyl]-1,2-Dithiin

To a stirred solution of 700 μL (502 mg; 5.02 mmol) of triethylamine in 5 mL THF at 0° C. was added cyclopentanecarbonyl chloride (250 μL; 272 mg, 2.06 mmol) followed by addition of 32 mg (0.18 mmol) of dithiin diol. After 5 min TLC showed the reaction to be complete. The reaction mixture was partitioned between 1M aqueous $H_3PO_4$ (50 mL) and diethyl ether (80 mL). The organic phase was washed with 10% aqueous solution of $NaHCO_3$ and water, then dried ($Na_2SO_4$). The organic phase was concentrated in vacuo and the crude product was purified on silica gel (diethyl ether-hexane, 1:3) to give 43 mg (64.3%) of the diester. $^1$H NMR ($CDCl_3$) δ6.368 (s, 2H), 4.711 (s, 4H), 2.781 (m, 2H), 1.893–1.580 (m, 16H); $^{13}$C NMR ($CDCl_3$) δ176.071, 130.715, 127.446, 65.030, 43.599, 29.953, 25.773; MS (EI) m/z=367.2 (100%; M-H).

The same product was obtained when the reaction was performed at −20° C. to −25° C.

Example 10

3-[(Cyclopentanecarbonyloxy)methyl]-6-hydroxymethyl-1,2-dithiin

To a stirred solution of TEA (0.35 mL, 500 mol %) in 5 mL THF, cooled to −45° C., cyclopentanecarbonyl chloride (25 μL, 120 mol %) was added followed by addition of 30 mg (0.17 mmol) of the dithiin diol. After 5 min, the reaction was complete. The reaction mixture was partitioned between 1M aqueous $H_3PO_4$ (50 mL) and ether (80 mL). The layers were separated and the organic phase was washed with 10% aqueous solution of NaHCO3, water and dried ($Na_2SO_4$). The organic phase was concentrated in vacuo and the residue was purified on silica gel (diethyl ether-hexane, 1:3) to give 25 mg (39.9%) of diester, identical to that isolated as described above.

Continued elution afforded 10 mg (21.6%) of the monoester: $^1$H NMR (CDCl$_3$) δ6.399 (s, 2H), 4.732 (s, 2H), 4.297 (d, J=4.4, 2H), 2.799 (t, J=8.0 Hz, 1H) 1.89–1.609 (m, 8H); $^{13}$C NMR (CDCl$_3$; 9 of 10 expected signal observed) δ136.026, 129.608, 127.787, 124.882, 65.204, 64.529, 43.637, 29.968, 25.788. MS (EI) m/z=272.0 (88%; M$^+$).

Example 11

3,6-Bis[(2-hydroxybenzoyloxy)methyl]-1,2-dithiin and 3-[(2'-hydroxybenzoyloxy)methyl]-6-hydroxymethyl-1,2-dithiin To a stirred solution of 3.5 g (20 mmol) of dithiin in 200 mL $CH_2Cl_2$ and 50 mL ethyl acetate was added 2.74 g (19.8 mmol) of salicylic acid and 4.50 g (21.8 mmol) of dicyclohexylcarbodiimide (DCC) and the reaction mixture was stirred under nitrogen at room temperature for 14 hours. TLC showed two new products, along with starting material. The TLC did not change after an additional 10 h reaction time. The reaction mixture was evaporated to a small volume, and applied to a silica gel column. Elution with ethyl acetate-hexane, 1:3 gave 40 mg (1.06 %) of the diester. $^1$H NMR (CDCl$_3$) δ7.878 (d, J=6.8 Hz, 2H), 7.489 (t, J=7.2 Hz, 2H), 7.001 (d, J=8.4 Hz, 2H), 6.909 (t, J=7.6 Hz, 2H), 6.517 (s, 4H); $^{13}$C NMR (CDCl$_3$) δ169.350, 161.817, 160.360, 136.117, 129.949, 128.068, 119.314, 117.691, 65.598, 61.183; MS (EI) m/z=416 (8%; M$^+$).

Continued elution afforded 1.68 g (28.4%; 62.4% based on recovered starting material) of the monosalicylate ester. $^1$H NMR (CDCl$_3$) δ7.878 (d, J=8.0 Hz, 1H), 7.487 (t, J=8.8 Hz, 1H), 6.987 (d, J=8.8 Hz, 1H), 6.909 (t, J=7.6 Hz, 1H), 6.458 (dd, J=20.8, 5.6 Hz, 2H), 4.987 (s, 2H), 4.301 (s, 2H); $^{13}$C NMR (CDCl$_3$) δ169.474, 161.721, 136.763, 136.126, 130.012, 128.585, 128.388, 124.747, 119.361, 117.646, 11.896, 65.909, 64.407; MS (LSIMS) m/z=296.0 (45 %; M$^+$).

Lastly, 2.0 g (57.1%) of starting material was isolated. When 110 mol% of carbonyldiimidazole (CDI) was used instead of DCC the yield of monoester was only 18.6%. The best yield of diester (14.1%) was obtained when 220 mol % salicylic acid and 220 mol % CDI were used, stirring the reaction mixture for 3 days at room temperature.

Example 12

3-[(tert-butyldimethylsilyloxy)methyl]-6-hydroxymethyl-1,2-dithiin (10)

To a stirred solution of 7.81 g (44.3 mmol) of dithiin 7 in 35 mL DMF was added imidazole (6.33 g, 210 mol%) followed by addition of TBDMS chloride (7.01 g, 105 mol %). In 20 hours stirring under nitrogen at room temperature TLC showed two new spots. The reaction mixture was chromatographed on silica gel (ethyl acetate-hexane, 1:3) to give 4.4 g (24.5%; 31.9% based on recovered starting material) of bis(TBDMS)ether. $^1$H NMR (CDCl$_3$) δ6.375 (s, 2H), 4.251 (s, 4H), 0.878 (s, 18H), 0.065 (s, 12H). 13C NMR (CDCl$_3$) δ134.387, 123.805, 64.9976, 25. 818, 18.354, −5.367.

Continued elution afforded 5.0 g (39%; 50.6% based on recovered starting material) of the monosilyl compound 10. $^1$H NMR (CDCl$_3$) δ6.337 (q, J=11.2 Hz, 2H), 4.261 (s, 2H), 4.238 (d, J=6.0 Hz, 2H), 0.881 (s, 9H), 0.070 (s, 6H). $^{13}$C NMR (CDCl$_3$) δ135.449, 133.977, 125.284, 123.676, 64.863, 64.643, 25.750, 18.285, −5.428; MS (LSIMS) m/z= 290.1 (M$^+$).

Elution with diethyl ether gave 1.81 g (23.2 % ) of unreacted diol.

Example 13

1-Hydroxy-6-(t-butyldimethylsilyloxy)-2,4-hexadiyne (8)

To a stirred solution of 1,6-dihydroxy-2,4-hexadiyne (5) (101 g; 920 mmol) in 300 mL of dimethyl formamide was added 125 g (1.84 mol) of imidazole and 138.3 g (0.917 mmol) of t-butyldimethysilylchloride. The resulting dark solution was stirred for 48 hours then it was diluted with 150 mL of water and 100 mL of saturated aqueous sodium chloride. This solution was extracted with diethyl ether (5×200 mL) and the combined organic phases were washed with water followed by saturated sodium chloride. The organic phase was dried (MgSO$_4$) and concentrated in vacuo to give a semisolid residue. The mixture was filtered and the solid was washed with 100 mL of a 1:1 diethyl ether-hexane mixture. The solid was air-dried and shown to be the starting diyne (10 g; 9.9% recovery) by TLC analysis. The filtrate was concentrated in vacuo and chromatographed over silica gel (ethyl acetate-hexane, 1:4) to give 66 g (21.3%) of the bis(silyloxy)diyne: $^1$H NMR (CDCl$_3$) δ4.373 (s, 4H, CH$_2$O), 0.899 (s, 18H, CCH$_3$), 0.118 (s, 12H, SiCH$_3$); $^{13}$C NMR (CDCl$_3$) δ77.592, 69.141, 52.020, 25.607, 18.172, −5.269.

Continued elution afforded 68 g (30.3%) of the monosilyloxy diyne 8: $^1$H NMR (CDCl$_3$) δ4.383 (s, 2H, CH$_2$O) 4.340 (s, 2H, CH$_2$O), 1.764 (br s, 1H, OH), 0.904 (s, 9H, CCH$_3$), 0.122 (s, 6H, SiCH$_3$); $^{13}$C NMR (CDCl$_3$; 8 of 9 expected carbons observed) δ78.328, 70.097, 68.838, 52.043, 51.451, 25.735, 18.240, −5.216.

Example 14

1-Hydroxy-6-(t-butyldimethylsilyloxy)-2,5-Bis[2'-(cyanoethyl)thio]-2,4-hexadiene (9)

To a stirred solution of 130 mg (2.31 mmol) of KOH in 400 μL of water was added 10 ml of DMF followed by the mercaptan HSCH$_2$CH$_2$CN (1.9 g, 500 mol %). The resulting clear solution was stirred under nitrogen for 25 minutes at room temperature, then 1.0 g (4.44. mmol) of 1-hydroxy-6-(t-butyldimethylsilyloxy)-2,4-hexadiyne (8) was added. The flask became slightly warm after 3 minutes. The reaction mixture was stirred for 16 hours at room temperature, after which time TLC showed the disappearance of the starting material. The reaction mixture was diluted with 40 mL of water and 50 mL of saturated aqueous sodium chloride. The solution was extracted with three 50-mL portions of ethyl acetate and the combined organic phases were washed with 100 mL of saturated aqueous sodium chloride. The organic phase was dried (MgSO$_4$) and concentrated in vacuo. The residue was chromatographed over silica gel (ethyl acetate-hexane, 1:3; then ethyl acetate-hexane, 1:1) to give 1.02 g (57%) of the unsymmetrical bis[(2-cyanoethyl)thio]adduct 9. $^1$H NMR (CD$_3$OD) δ7.25 (q, J=24, 17 Hz, 2H), 7.02 (d, J=10, 6.8 Hz, 1H), 6.75 (d, J=10, 6.8 Hz, 1H), 4.35 (m, 4H), 2.9 (m, 8H), 0.977 (m, 9H), 0.156 (s, 6H); $^{13}$C NMR (CD$_3$OD) δ138.923, 137.975, 123.767, 119.777, 68.049, 66.683, 63.573, 28.678, 19.514, −5.011.

Example 15

3-[(tert-butyldimethylsilyloxy)methyl]-
6-hydroxymethyl-1,2-dithiin (10)

To a stirred solution of the bis(2'-cyanoethyl)butadiene 9 from Example 14 (4.60 g; 11.5 mmol) in 300 mL of dry diethyl ether was added 13 g (116 mmol) of solid potassium t-butoxide. The reaction mixture was stirred for 10 minutes at room temperature, then 325 mL of water was added, followed by a solution of 8.37 g (25.4 mmol) of potassium ferrocyanide in 140 mL of water. The reaction mixture was stirred for 10 minutes at room temperature then it was extracted with diethyl ether (5×500 mL). The combined ether layers were washed with water, dried (Na$_2$SO$_4$) and concentrated in vacuo. The residue was chromatographed over silica gel (ethyl acetate-hexane, 1:6) to give 1.39 g (41.5%) of the title compound. This material was identical by spectroscopic and TLC analysis to the material isolated from 3,6-bis(hydroxymethyl)-1,2-dithiin 7 (Example 12).

Example 16

3-Azidomethyl-6-[(tert-butyldimethylsilyloxy)
methyl]-1,2-dithiin (15)

To a stirred solution of 3.4 g (11.7 mmol) of 3-[(tert-butyldimethylsilyloxy)methyl]-6-hydroxymethyl-1,2-dithiin (10) in 12 mL of toluene was added diphenylphosphoryl azide (3.02 mL; 3.86 g, 14.0 mmol) in 8 mL of toluene and the solution was cooled to 0° C. To the cold solution was added dropwise 2.09 mL (2.13 g; 14.0 mmol) of DBU. The reaction mixture became dark. In 2 hours at 0° C., the reaction mixture was allowed to warm up to room temperature. After 14 hours the reaction mixture was purified on a silica gel column using 5% ethyl acetate in hexane to give 2.75 g (74.5%) of azide 15. $^1$H NMR (CDCl$_3$) δ6.38 (m, 2H, C=CH), 4.30 (s, 2H, CH$_2$O), 3.98 (s, 2H, CH$_2$O), 0.92 (s, 9H, CCH$_3$), 0.10 (s, 6H, SiCH$_3$). $^{13}$C NMR (CDCl$_3$) δ136.898 128.007, 123.471, 64.726, 55,145, 25.780, 25.735, 18.278, −5.443; MS (EI) m/z=315.1 (100%; M$^+$).

Example 17

3-Asidomethyl-6-hydroxymethyl-1,2-dithiin (27)

To a stirred solution of 62 mg (19.7 mmol) of the (silyloxy)azide 15 in 1.5 mL acetonitrile was added 1.5 mL of a 1:3 mixture of 30% aqueous hydrofluoric acid in CH$_3$CN. After 5 minutes, TLC analysis showed no remaining starting material. The reaction mixture was neutralized with a saturated aqueous K$_2$CO$_3$ solution and extracted with ethyl acetate. The organic extract was washed with water, dried over Na$_2$SO$_4$ and purified on a silica gel column to give 24.4 mg (61.9%) of the title compound. $^1$H NMR (CDCl$_3$) δ6.44 (m, 2H), 4.30 (d, J=6.0 Hz, 2H), 3.99 (s, 2H); $^{13}$C NMR (CDCl$_3$) δ136.429, 128.661, 127.948, 124.929, 64.468, 55.091; MS (LSIMS) m/z=201.0 (100%; M$^+$).

Example 18

3-[(N-(4-methylbenzenesulfonamido)carbonyl)oxy]-
6-(tert-butyldimethylsilyloxymethyl)-
1,2-Dithiin (13)

To a stirred solution of 100 mg (0.344 mmol) of 3-[(tert-butyldimethylsilyloxy)methyl]-6-hydroxymethyl-1,2-dithiin (10) in 2 mL of dry tetrahydrofuran was added 408 mg (2.07 mmol) of 4-methylbenzenesulfonyl isocyanate in 500 μL of dry tetrahydrofuran. After 5 minutes TLC analysis showed complete consumption of starting material. The reaction mixture was chromatographed directly on silica gel (ethyl acetate-hexane, 1:3) to give 110 mg (66.6%) of N-sulfonylcarbamate 13. $^1$H NMR (CDCl$_3$; spectrum shows amide bond isomers) δ7.928 (d, J=8.0 Hz, 2H, ArH), 7.340 (d, J=8.4 Hz, 2H, ArH), 6.316 (s, 2H, C=CH), 4.676 (s, 2H, CH$_2$O), 4.271 (s, 2H, CH$_2$O), 2.440 (s, 3H, ARCH$_3$), 0.908 (s, 9H, CCH$_3$), 0.093 (s, 6H, SiCH$_3$).

Example 19

3-[(N-(4-methylbenzenesulfonamido)carbonyl)oxy]-
6-(hydroxymethyl)-1,2-Dithiin (14)

To a stirred solution of 27 mg (0.055 mmol) of the above compound in 1.0 mL of acetonitrile was added 1.0 mL of a 1:3 mixture of 30% aqueous hydrofluoric acid and acetonitrile. The solution was shaken for 5 minutes then the solution was neutralized with saturated aqueous potassium carbonate. The reaction mixture was extracted with ethyl acetate and the ethyl acetate solution was applied to a column of silica gel and eluted with ethyl acetate-hexane, 1:1 to give 5 mg of the title compound. $^1$H NMR (CDCl$_3$; spectrum shows amide bond isomers) δ7.934 (d, J=8.4 Hz, 2H, ArH), 7.355 (d, J=8.0 Hz, 2H, ArH), 6.353 (q, J=5.2 Hz, 2H, C=CH), 5.195 (s, CH$_2$O), 4.791 (s, CH$_2$O), 4.692 (s, CH$_2$O), 4.284 (s, CH$_2$O), 2.454 (s, 3 H, ARCH$_3$).

Example 20

3-(Acetamido)methyl-6-[(tert-butyldimethylsilyloxy)
methyl]-1,2-dithiin (19)

To a stirred solution of 94 mg (0.328 mmol) of the silyloxy azide in 1.8 mL of dry tetrahydrofuran was added 100 μL (107 mg; 1.06 mmol) of acetic anhydride followed by 25 μL of water and 120 mg (0.457 mmol) of triphenylphosphine. After three hours, TLC analysis showed complete consumption of starting material. The reaction mixture was partitioned between 25 mL of water and 40 mL of ethyl acetate. The layers were separated and the aqueous phase was extracted with two 40-mL portions of ethyl acetate. The combined organic phases were washed with two 50-mL portions of saturated aqueous sodium chloride. The organic layer was dried (Na$_2$SO$_4$) and concentrated in vacuo to give an orange-brown oil. This material was chromatographed over 20 g of silica gel (ethyl acetate-hexane, 5:2) to give 36 mg of a semisolid mixture.

Continued elution afforded 58 mg of a yellow-brown oil which was contaminated with triphenylphosphine oxide. Repurification of this material on silica gel (ethyl acetate-hexane, 5:2) afforded 38 mg (35%) of amide 19. $^1$H NMR (CDCl$_3$; spectrum shows amide bond isomers) δ6.796 (d, J=3.2 Hz, 1H, C=CH; minor isomer), 6.745 (d, J=3.6 Hz, 1H, C═CH minor isomer), 6.309 (br t, J=7.2 Hz, 2H, C═CH; major isomer), 5877 (br s, 1H, NH), 4.802 (s, 2H, CH$_2$O; minor isomer), 4.542 (d, J=5.6, 2H, CH$_2$N; minor isomer), 4.277 (s, 2H, CH$_2$O; minor isomer), 4.056 (d, J=6.0 Hz, 2H, CH$_2$N; major isomer), 2.034 (s, 3H, COCH$_3$; major isomer), 2.005 (s, 3H, COCH$_3$; minor isomer), 0.914 (s, 9H, CCH$_3$), 0.095 (s, 6H, SiCH$_3$); $^{13}$C NMR (CDCl$_3$, spectrum shows amide bond isomers) δ170.094 (major isomer), 169.654 (minor isomer), 145.258 (minor isomer), 139.887 (minor isomer), 135.085 (major isomer), 131.406 (major isomer), 126.627 (major isomer), 125.641 (minor isomer), 123.790 (major isomer), 123.524 (minor isomer), 64.832 (major isomer), 60.766 (minor isomer), 43.698 (major isomer), 38.646 (minor isomer), 25.833 (minor isomer), 25.742 (major isomer), 23.171, 18.293, −5.307 (minor isomer), −5.420 (major isomer); MS (LSIMS) m/z=73.0 (100%), 331 (M$^+$).

Example 21

3-(Acetamido)methyl-6-hydroxymethyl-1,2-dithiin (20)

To a stirred solution of 52 mg (0.152 mmol) of the (silyloxy)amide 19 in 1.0 mL of acetonitrile, previously cooled in an ice-water bath, was added 500 μL of a 1:3 solution of 30% aqueous hydrofluoric acid solution in acetonitrile. The resulting solution was stirred for 15 minutes in the ice bath, after which time TLC analysis showed the reaction to be complete. The acid was neutralized by cautious addition of about 15 mL of a 10% aqueous potassium carbonate solution to the reaction mixture. The reaction mixture was partitioned between 20 mL of water and 40 mL of ethyl acetate. The layers were separated and the aqueous phase was extracted with 40 mL of ethyl acetate. The combined organic phases were washed with two 50-mL portions of saturated aqueous sodium chloride, dried (Na$_2$SO$_4$) and concentrated in vacuo. The residue (33 mg) was chromatographed over 20 g of silica gel (ethyl acetate) to give 24 mg (71%) of acetamide 20 as an orange oil. $^1$H NMR (CDCl$_3$) δ6.792 (m, 2H, C═CH; minor isomer), 6.309 (d, J=6.4 Hz, 1H, C═CH; major isomer), 6.269 (d, J=5.6 Hz, 1H, C═CH; major isomer), 6.82 (br s, 1H, NH), 4.276 (br s, 2H, CH$_2$O; minor isomer), 4.512 (d, J=5.6 Hz, 2H, CH$_2$N; minor isomer), 4.228 (br s, 2H, CH$_2$0; major isomer), 4.023 (d, J=6.0 Hz, 2H, CH$_2$N; major isomer), 2.05 (s, 1H, OH), 1.998 (s, 3H, COCH$_3$; major isomer); $^{13}$C NMR (CDCl$_3$) δ170.116, 144.100 (minor isomer), 141.214 (minor isomer), 134.827 (major isomer), 132.384 (major isomer), 126.528 (major isomer), 125.815 (minor isomer), 125.254 (minor isomer), 125.178 (major isomer), 64.499 (major isomer), 60.099 (minor isomer), 43.690 (major isomer), 38.631 (minor isomer), 23.140 (major isomer), 21.011 (minor isomer); MS (LSIMS) m/z=57 (100%), 217 (M$^+$).

Example 22

3-(2'-Hydroxybenzamido)methyl-6-[(tert-butyldimethylsilyloxy)methyl]-1,2-dithiin (22)

To a stirred solution of the azidomethyl dithiin (194 mg; 0.616 mmol) in 3.0 mL of dry tetrahydrofuran was added 50 μL of water, followed by triphenylphosphine (220 mg; 0.839 mmol) and 4H-1,3-benzodioxin-2,4-dione (21) (260 mg; 1.59 mmol). The reaction mixture was stirred for 2.5 hours after which time TLC analysis showed no starting material to be present. The reaction mixture was diluted with ethyl acetate (50 mL) and this solution was washed with two portions of 10% aqueous sodium hydrogen carbonate solution (30 mL) followed by two portions of saturated aqueous sodium chloride (30 mL). The organic phase was dried (Na$_2$SO$_4$) and concentrated in vacuo to give an orange oil. This material was chromatographed over 30 g of silica gel (ethyl acetate-hexane, 1:4) to give 55 mg (22%) of the benzamide 22 as an orange solid. $^1$H NMR (CDCl$_3$) δ12.093 (s, 1H, ArOH), 7.480–7.350 (m, 1H, ArH), 7.011 (d, J=8.0 Hz, 1H, ArH), 6.881 (t, J=7.6 Hz, 1H, ArH), 6.607 (br s, 1H, NH), 6.379 (dd, J=15.2, 6.4 Hz, 2H, C═CH), 4.301 (s, 2H, CH$_2$O), 4.273 (d, J=6 Hz, 2H, CH$_2$N), 0.923 (s, 9H, CCH$_3$), 0.111 (s, 6H, SiCH$_3$); $^{13}$C NMR (CDCl$_3$) δ169.942, 161.597, 135.692, 134.554, 130.397, 127.150, 125.405, 123.706, 118.783, 118.707, 64.810, 43.577, 25.765, 18.316, −5.398; MS (LSIMS) m/z=75 (100%), 409.1 (M$^+$).

Example 23

3-(2'-Hydroxybenzamido)methyl-6-hydroxymethyl-1,2-dithiin (23)

To a stirred solution of the above (silyloxy)amide 22 (52 mg; 0.127 mmol) in 2.0 mL of acetonitrile was added 2.0 mL of a 1:3 solution of 30% aqueous hydrofluoric acid solution in acetonitrile. The resulting orange solution was stirred for 40 minutes in the ice bath then the excess acid was destroyed by the addition of about 10 mL of a 10% aqueous potassium carbonate solution. The reaction mixture was partitioned between 50 mL of ethyl acetate and 20 mL of saturated aqueous sodium chloride. The layers were separated and the aqueous phase was extracted with 50 mL of ethyl acetate. The combined organic phases were washed with 50 mL of saturated aqueous sodium chloride, dried (Na$_2$SO$_4$) and concentrated in vacuo. The residue (35 mg) was chromatographed over 20 g of silica gel (ethyl acetate-hexane, 1:1) to give 24.4 mg (65%) of the benzamide as an orange oil. $^1$H NMR (CD$_3$OD; spectrum shows amide bond isomers) δ7.773 (dd, J=8.0, 1.6 Hz, 1H, ArH), 7.383 (dt, J=8.4, 1.6 Hz, 1H, ArH), 6.925–6.860 (m, 2H, ArH), 6.371 (br s, 2H, C═CH), 4.691 (s, 2H, CH$_2$; minor isomer), 4.669 (s, 2H, CH$_2$; minor isomer), 4.198 (s, 2H, CH$_2$; major isomer), 4.173 (s, 2H, CH$_2$; major isomer); $^{13}$C NMR (CD$_3$OD; spectrum shows amide bond isomers) δ170.987, 161.079, 136.252, 134.962, 133.294, 129.055, 127.061, 125.984, 120.175, 118.424, 116.816, 64.778 (major isomer), 60.079 (minor isomer), 44.033 (major isomer), 39.112 (minor isomer); MS (LSIMS) m/z=55.0 (100%), 295.1 (M$^+$).

Example 24

3-Azidomethyl-6-chloromethyl-1,2-Dithiin (28)

To a stirred solution of the silyloxyazide 15 (100 mg; 0.31 mmol) in distilled THF (5 mL) was added at room temperature water (6.7 μL), followed by the sequential addition, in one portion, of triphenylphosphine (97 mg; 0.37 mmol) and triphosgene (460 mg; 1.55 mmol). The reaction mixture was shielded from light and stirred at room temperature overnight. The reaction mixture was chromatographed on silica gel, eluting with 10% ethyl acetate in hexane, to afford 27.4 mg (40.4%) of the title chloride 28. $^1$H NMR (CDCl$_3$) δ6.425 (dd, J=6.4, 6.0 Hz, 2H, C═CH), 4.267 (s, 2H, CH$_2$), 4.004 (s, 2H, CH$_2$); $^{13}$C NMR (CDCl$_3$) δ128.538, 28.417, 127.719, 127.582, 54.864, 46.634.

Example 25

1-(Tert-butyldimethylsilyloxy)-2-Hydroxybenzene (16)

To a stirred solution of catechol (5.5 g; 50 mmol) in 20 mL of dimethylformamide was added imidazole (7.14 g; 105 mmol) and t-butyldimethylsilylchloride (7.53 g; 50 mmol). The reaction mixture was stirred for 3 hours after which time TLC showed the reaction to be complete. The reaction mixture was chromatographed directly onto silica gel and eluted with 5% ethyl acetate in hexane to give 7.4 g (66%) of the monosilyl catechol 16. NMR (CDCl$_3$) δ6.963 (dd, J=8.0, 1.6 Hz, 1H, ArH), 6.891 (dt, J=8.0, 2.0 Hz, 1H, ArH), 6.847 (dd, J=8.0, 1.6 Hz, 1H, ArH), 6.773 (dt, J=7.6, 1.6 Hz, 1H, ArH), 5.518 (s, 1H, OH), 0.996 (s, 9H, CCH$_3$), 0.252 (s, 6H, SiCH$_3$); $^{13}$C NMR (CDCl$_3$) δ147.250, 142.550, 122.143, 119.989, 117.835, 114.870, 25.730, 18.193, −4.322.

Example 26

3-[2'-(Tert-butyldimethylsilyloxy)phenyloxy]methyl-6-(tert-butyldimethylsilyloxy)methyl-1,2-Dithiin (17)

To a stirred solution of 200 mg (0.688 mmol) of monosilyl dithiin 10 in 2 mL of dry tetrahydrofuran, was added a solution of the monosilyl catechol from Example 26 (310 mg; 1.38 mmol) in 1 mL of dry tetrahydrofuran, followed by 220 mg (0.839 mmol) of triphenylphosphine. The resulting solution was cooled to 5° C., then 140 μL (155 mg; 890 mmol) of diethyl azodicarboxylate was added. After 3 hours, TLC analysis showed the reaction to be complete. The reaction mixture was chromatographed directly on silica gel (ethyl acetate-hexane, 1:6) to give 213 mg (62.3%) of the protected ether 17. $^1$H NMR (CDCl$_3$) δ6.865–6.820 (m, 4H, ArH), 6.411 (d, J=6.4 Hz, 1H, C═CH), 6.320 (d, J=5.6 Hz, 1H, C═CH), 4.611 (s, 2H, CH$_2$O), 4.264 (s, 2H, CH$_2$O), 0.977 (s, 9H, CCH$_3$), 0.887 (s, 9H, CCH$_3$), 0.153 (s, 6H, SiCH$_3$), 0.075 (s, 6H, SiCH$_3$); $^{13}$C NMR (CDCl$_3$) d 149.510, 145.635, 135.944, 129.384, 127.087, 123.500, 122.127, 121.688, 121.286, 115.249, 70.759, 64.829, 25.776, 25.745, 18.322, −4.511, −5.391; MS (LSIMS) m/z= 273.2 (100%), 496.4 (M$^+$).

Example 27

3-[(2'-Hydroxy)phenyloxy]methyl-6-hydroxymethyl-1,2-Dithiin (18)

To a stirred solution of the protected ether (150 mg; 0.302 mmol) in 2 mL of dry tetrahydrofuran was added a mixture of 2.65 mL of 1M tetrabutylammonium fluoride in tetrahydrofuran and 1.7 mL of acetic acid. The reaction mixture was stirred for 4 hours, concentrated in vacuo and the residue partitioned between 20 mL of water and 30 mL of ethyl acetate. The organic phase was washed with dilute aqueous sodium bicarbonate, water and dried (Na$_2$SO$_4$). The residue was chromatographed over silica gel (ethyl acetate-hexane, 1:3) to give 50 mg (62.5%) of the dithiin 18. $^1$H NMR (CD$_3$OD; sample shows doubling of signals) δ6.985–6.915 (m, 1H, ArH), 6.850–6.795 (m, 2H, ArH), 6.765–6.715 (m, 1H, ArH), 6.486 (br d, J=5.6 Hz, 1H, C═CH), 6.379 (br d, J=6.0 Hz, 1H, C═CH), 5.245 (s, 2H, CH$_2$O; minor isomer), 4.881 (s, 2H, CH$_2$O; major isomer), 4.693 (s, 2H, CH$_2$O; minor isomer), 4.179 (s, 2H, CH$_2$O; major isomer); MS (LSIMS) m/z=71.0 s (100% ), 268.1 (M$^+$).

Example 28

2-(t-Butyldimethylsilyloxy)phenyl Isocyanate (24)

To a stirred solution of 1.0 g (9.16 mmol) of o-aminophenol in 10 mL of tetrahydrofuran was added 3.57 mL (2.59 g; 25.6 mmol) of triethylamine and 3.46 g (22.9 mmol) of t-butyldimethylsilyl chloride. The reaction mixture was stirred for 15 hours at room temperature, filtered and concentrated in vacuo. The residue was dissolved in 10 mL of toluene and this solution was cooled to −15° C. The solution was treated with 1.4 mL (1.02 g; 10.0 mmol) of triethylamine, followed by the dropwise addition of 4.75 mL (9.17 mmol) of a 1.93M solution of phosgene in toluene. After the addition was complete, the reaction mixture was allowed to warm up to room temperature and stirred at that temperature for 1 hour. The mixture was filtered and the filtrate was concentrated in vacuo to give a pink oil. IR (neat) 2251 cm$^{-1}$; $^1$H NMR (CDCl$_3$) δ7.060 (dt, J=8.4, 2.0 Hz, 1H, ArH), 7.018 (dd, J=7.6, 2.0 Hz, 1H, ArH), 6.950–6.850 (m, with d at 6.894, J=7.6 Hz, 2H, ArH), 1.08 (s, 9H, CCH$_3$), 0.350 (s, 6H, SiCH$_3$); MS (EI) m/z=192 (100%), 249 (M$^+$).

Example 29

Silylated Carbamate 30

To a stirred solution of 230 mg (0.924 mmol) of the above isocyanate (24) in 1 mL of dry tetrahydrofuran was added 143 μL (104 mg; 1.03 mmol) of triethylamine followed by a solution of 230 mg (0.792 mmol) of the monoprotected diol 10. The reaction mixture was stirred at room temperature for 15 hours then it was chromatographed over silica gel (5% ethyl acetate in hexane to give 375 mg (87%) of the carbamate 30 as an orange oil. $^1$H NMR (CDCl$_3$; spectrum shows amide bond isomers) δ8.030 (br s, 1H, NH), 7.194 (br s, 1H, OH), 6.991–6,895 (m, 3H, ArH), 6.830–6.800 (m, 1H, ArH), 6.432 (d, J=6.0 Hz, 1H, C═CH), 6.380 (d, J=6.0 Hz, 1H, C═CH), 5.311 (s, 2H, CH$_2$O; minor isomer), 4.849 (s, 2H, CH$_2$O; minor isomer), 4.824 (s, 2H, CH$_2$O; major isomer), 4.306 (s, 2H, CH$_2$O; major isomer), 1.099 (s, 9H, CCH$_3$), 0.938 (s, 9H, CCH$_3$), 0.262 (s, 6H, SiCH$_3$), 0.115 (s, 6H, SiCH$_3$); MS (LSIMS) m/z=74.6 (100%), 539.3 (M$^+$).

Example 30

3-[(2'-(Hydroxyphenyl)amino)carbonyloxy]methyl-6-hydroxymethyl-1,2-Dithiin (31)

To a stirred solution of silyl carbamate 30 (58 mg; 0.109 mmol) in 1 mL of dry tetrahydrofuran was added a mixture of 1.2 mL of a 1M solution of tetrabutylammonium fluoride in tetrahydrofuran and 700 μL of acetic acid. The mixture was stirred for 2 hours after which time it was done by TLC. The reaction mixture was concentrated in vacuo, partitioned between 20 mL of water and 30 mL of ethyl acetate. The organic phase was washed with dilute aqueous sodium bicarbonate, water, dried (Na$_2$SO$_4$) and concentrated in vacuo. The residue was chromatographed over silica gel (ethyl acetate-hexane, 1:3) to give 25 mg (75%) of the deprotected carbamate 31. 1H NMR (CDCl$_3$; spectrum shows amide bond isomers) d 7.701 (br s, 1H, NH), 6.995–6.902 (m, 2H, ArH), 6.847–6.794 (m, 2H, ArH), 6.522 (d, J=6.0 Hz, 1H, C═CH), 6.433 (d, J=6.4 Hz, 1H, C═CH), 5.311 (s, 2H, CH$_2$O; minor isomer), 4.808 (s, 2H, CH$_2$O; major isomer), 4.725 (s, 2H, CH$_2$O; minor isomer), 4.210 (s, 2H, CH$_2$O; major isomer).

Antifungal Activity

The antifungal activities of the dithiins listed below were determined in vitro using three fungal cultures-Candida albicans (CA), *Cryptococcus neoformans* (CN), and *Aspergillus fumigatus* (AF), and the minimum inhibitory concentration (MIC) for each is summarized in Table I. Table II shows MIC data on selected dithiins for the fungal cultures of Candida krusei (CK), Candida parapsilosis (CP), Candida tropicalis (CT), and Trichophyton. rubrum (TR). The method used to determine in vitro antifungal activity is discussed in McGinnis, M. R., *Laboratory Handbook of Medical Mycology*, Academic Press, New York, London, pp. 412–416 (1980); and Drouget, E.; Dupont, B.; Improvisi, L.; Vivian, M. A.; and Tortorano, A. M.; "disc agar diffusion and microplate automatized techniques for in vitro evaluation of antifungal agents on yeast and sporulated pathogenic fungi" in In Vitro and In Vivo Evaluation of Antifungal Agents, Eds. Iwata, K. and Vanden Bossche, H., Elsevier Science Publishers, New York, Oxford, p 303 (1986).

TABLE I

Antifungal Activity of the Dithiin Derivatives

| Dithiin Derivative | Mic (μg/mL) | | |
|---|---|---|---|
| | CA | CN | AF |
| 3,6-Bis[(4-pyridylcarbonyl-oxy)methyl]-1,2-Dithiin | 2 | NT | 2 |
| 3,6-Bis[(3'-pyridylcarbonyl-oxy)methyl]-1,2-Dithiin | 4 | NT | 2 |
| 3,6-Bis(cyclopentanecar-bonyloxy)methyl]-1,2-Dithiin | >250 | NT | >250 |
| 3-[(cyclopropylcarbonyl-oxy)methyl]-6-(hydroxymethyl)-1,2 Dithiin | 0.63 | 0.63 | 1.25 |
| 3-(acetyloxymethyl)-6-(hydroxymethyl)-1,2 Dithiin | 0.63 | 0.31 | 0.31 |
| 3-[(4-pyridylcarbonyloxy)methyl]-6-hydroxymethyl-1,2-dithiin | 3.1 | NT | 1.6 |
| 3-[(Cyclopentanecarbonyl-oxy)methyl]-6-hydroxymethyl-1,2-dithiin | 6.3 | NT | 3.1 |
| 3,6-Bis[(2'-hydroxybenzoyloxy)-methyl]-1,2-dithiin | >250 | NT | 250 |
| 3-[(2'-hydroxybenzoyl-oxy)methyl]-6-hydroxymethyl-1,2-dithiin | 0.2 | 0.2 | 0.2 |
| 3-Azidomethyl-6-hydroxymethyl-1,2-dithiin | 0.25 | ≦0.25 | ≦0.25 |
| 3-[(N-(4-methylbenzenesulfon-amido)-carbonyl)oxy]-6-(hydroxymethyl)-1,2-dithiin | 100 | 50 | 100 |
| 3-(Acetamido)methyl-6-hydroxy-methyl-1,2-dithiin | >100 | 100 | >100 |
| 3-(2'-Hydroxybenzamido)methyl-6-hydroxymethyl-1,2-dithiin | >100 | 50 | >100 |
| 3-Azidomethyl-6-chloromethyl-1,2-Dithiin | 25 | 6.3 | 50 |
| 3-[(2'-Hydroxy)phenyloxy]methyl-6-hydroxymethyl-1,2-Dithiin | 6.3 | 25 | 12.5 |

TABLE II

Antifungal Activity of Selected Dithiin Derivatives for Other Fungi

| Dithiin Derivative | MIC (μg/mL) | | | |
|---|---|---|---|---|
| | CK | CP | CT | TR |
| [(cyclopropylcarbonyloxy)methyl]-6-(hydroxymethyl)-1,2-Dithiin | 1.25 | 2.50 | 1.25 | 0.31 |

TABLE II-continued

Antifungal Activity of Selected Dithiin Derivatives for Other Fungi

| Dithiin Derivative | MIC (μg/mL) | | | |
|---|---|---|---|---|
| | CK | CP | CT | TR |
| 3-(Acetyloxymethyl)-6-(hydroxymethyl)-1,2-Dithiin | 1.25 | 1.25 | 1.25 | 0.31 |

NT = Not Tested

All references cited in the present application are incorporated by reference in their entirety.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed:

1. A method of synthesizing a 3,6-disubstituted-1,2-dithiin comprising the steps of:

(a) reacting a thiol or thiolate with a symmetrical or unsymmetrical 1,3-diyne to form a bis(alkylthio)butadiene, said thiol having the structure:

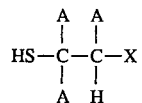

and said thiolate having the structure:

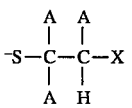

wherein each A is independently selected from the group consisting of hydrogen, $C_1$–$C_{10}$ alkyl, $C_3$–$C_{10}$ cycloalkyl, phenyl, 2-pyridyl, 3-pyridyl and 4-pyridyl; each phenyl, 2-pyridyl, 3-pyridyl and 4-pyridyl is optionally and independently substituted with one or more groups selected from the group consisting of halogen, nitro, cyano, trifluoromethyl, $C_1$–$C_{10}$ alkyl, $C_3$–$C_{10}$ cycloalkyl, —C(O)O$C_1$–$C_{10}$ alkyl and —C(O)N(B)(B), each B being independently selected from the group consisting of hydrogen and $C_1$–$C_{10}$ alkyl;

X is selected from the group consisting of cyano, nitro, —CHO, —S(O)$_m$$C_1$–$C_{10}$ alkyl, —P(O) O$C_1$–$C_{10}$ alkyl, —C(O)O$C_1$–$C_{10}$ alkyl and —C(O)N(B)(B), wherein m=1–2;

(b) treating the bis(alkylthio)butadiene with a base to generate a bis(thiyl)butadiene dianion; and (c) treating the bis(thiyl)butadiene dianion with an oxidizing agent to form a 3,6-disubstituted-1,2-dithiin.

2. The method of claim 1, wherein the 1,3-diyne is 1,6-dihydroxy-2,4-hexadiyne or a derivative of 1,6-dihydroxy-2,4-hexadiyne wherein one or both of the hydroxyl groups thereof is protected with a protecting group, said protecting group selected from the group consisting of acetyl, benzoyl, triethylsilyl, trimethylsilyl, triisopropylsilyl, dimethylisopropylsilyl, diethylisopropylsilyl, benzyl, tert-butyldimethylsilyl, tert-butyldiphenylsilyl, allyl, methoxyethoxyethyl, triphenylmethyl, tetrahydropyranyl, diphenylmethyl, p-methoxybenzyl, 3,4-dimethoxybenzyl, tert-butyl, tert-butyloxymethyl, 2-(trimethylsilyl)ethoxymethyl, methoxymethyl, 2-(trimethylsilyl)ethyl, dimethylthexylsilyl, benzyloxymethyl, p-methoxybenzyloxymethyl, (4-methoxyphenoxy)methyl, methylthiomethyl, 2,2,2-tricholorethoxymethyl, tribenzylsilyl, triphenylsilyl, diphenylmethylsilyl, tert-butylmethoxyphenylsilyl, tetrahydrofuranyl and 2,2,2-trichloroethyl.

3. The method of claim 1, wherein the thiol is reacted with the 1,3-diyne in the presence of an alkali metal hydroxide.

4. The method of claim 3, wherein the alkali metal hydroxide is potassium hydroxide.

5. The method of claim 1 further comprising reacting the thiol or thiolate with the symmetrical or unsymmetrical 1,3-diyne in a reaction solvent selected from the group consisting of tetrahydrofuran, diethyl ether, diisopropyl ether, t-butyl methyl ether, t-butyl ethyl ether, ethylene glycol, ethylene glycol methyl ether, diethylene glycol methyl ether, dichloromethane, dichloroethane, dimethylformamide, methanol, ethanol, benzene, toluene, dimethylacetamide, dimethylsulfoxide, N-methylpyrrolidinone, water, and mixtures thereof.

6. The method of claim 1 wherein said base is selected from the group consisting of sodium amide, potassium amide, lithium amide, sodium hydride, n-butyllithium, s-butyllithium, phenyllithium, triphenylmethyllithium, t-butyllithium, potassium t-butoxide, sodium t-butoxide, sodium methoxide, sodium s-butoxide, lithium diisopropylamide, sodium diisopropylamide, potassium diisopropylamide, sodium bis(trimethylsilyl)amide, potassium bis(trimethylsilyl)amide, lithium bis(trimethylsilyl)amide, lithium isopropylcyclohexylamide, potassium isopropylcyclohexylamide, sodium isopropylcyclohexylamide, 1,8-diazabicyclo[5.4.0]undec-7-ene, 1,5-diazabicyclo[4.3.0]non-5-ene, 1,4-diazabicyclo[2.2.2]octane, potassium carbonate, sodium carbonate and mixtures thereof.

7. The method of claim 5, wherein said solvent is dimethylformamide.

8. The method of claim 6 wherein said base is potassium t-butoxide.

9. The method of claim 1, wherein the thiol is selected from the group consisting of 2-(cyanoethyl)mercaptan, 2-(nitroethyl)mercaptan, methyl 3-thiopropionate and ethyl 3-thiopropionate.

10. The method of claim 1, wherein the oxidizing agent is selected from the group consisting of bromine, chlorine, iodine, osmium tetroxide, potassium permanganate, peracetic acid, trifluoroperacetic acid, m-chloroperbenzoic acid, N-bromosuccinimide, N-chlorosuccinimide, N-iodosuccinimide, sodium periodate, potassium periodate, potassium peroxymonosulfate, potassium dichromate, pyridinium chlorochromate, pyridinium dichromate, potassium ferrocyanide, potassium ferrocyanide trihydrate, potassium superoxide, hydrogen peroxide, bis(trimethylsilyl)peroxide, lead tetraacetate, lithium perchlorate, lithium peroxide, manganese dioxide, nickel(II) oxide, nickel peroxide, potassium chromate, sodium nitrate, potassium nitrate, nitric acid, silver(i) oxide, silver(II) oxide, sodium percarbonate, sodium perchlorate, lithium perchlorate, sodium peroxide, tetrabutylammonium chlorochromate, tetrabutylammonium periodate and benzoyl peroxide.

11. The method of claim 10 wherein oxidizing agent is potassium ferrocyanide trihydrate.

12. The method of claim 1, wherein the thiol is 2-(cyanoethyl)mercaptan.

13. The method of claim 12, wherein the 1,3-diyne is 1,6-dihydroxy-2,4-hexadiyne.

14. The method of claim 13, wherein the oxidizing agent is potassium ferrocyanide trihydrate.

15. The method of claim 1 further comprising treating the bis(thiyl)butadiene dianion with an oxidizing agent in the presence of a reaction solvent selected from the group consisting of tetrahydrofuran, diethyl ether, diethylether and water, diisopropyl ether, t-butyl methyl ether, t-butyl ethyl ether, ethylene glycol, ethylene glycol methyl ether, diethylene glycol methyl ether, dichloromethane, dichloroethane, dimethylformamide, methanol, ethanol, t-butanol, benzene, toluene, dimethylacetamide, dimethylsulfoxide, N-methylpyrrolidinone and mixtures thereof.

16. The method of claim 15, wherein the reaction solvent is diethyl ether or a mixture of diethyl ether and water.

* * * * *